United States Patent
Burghes et al.

(10) Patent No.: US 9,725,716 B2
(45) Date of Patent: Aug. 8, 2017

(54) NON-IONIC, LOW OSMOLAR CONTRAST AGENTS FOR DELIVERY OF ANTISENSE OLIGONUCLEOTIDES AND TREATMENT OF DISEASE

(71) Applicants: OHIO STATE INNOVATION FOUNDATION, Columbus, OH (US); RESEARCH INSTITUTE AT NATIONWIDE CHILDREN'S HOSPITAL, Columbus, OH (US)

(72) Inventors: Arthur Burghes, Columbus, OH (US); Paul Porensky, Worthington, OH (US); Brian Kaspar, New Albany, OH (US)

(73) Assignee: Ohio State Innovation Foundation and Research Institute at Nationwide Children's Hospital, Columbus, OH (US)

( * ) Notice: Subject to any disclaimer, the term of this patent is extended or adjusted under 35 U.S.C. 154(b) by 52 days.

(21) Appl. No.: 14/363,670

(22) PCT Filed: Dec. 6, 2012

(86) PCT No.: PCT/US2012/068267
§ 371 (c)(1),
(2) Date: Jun. 6, 2014

(87) PCT Pub. No.: WO2013/086207
PCT Pub. Date: Jun. 13, 2013

(65) Prior Publication Data
US 2014/0323552 A1    Oct. 30, 2014

Related U.S. Application Data

(60) Provisional application No. 61/567,416, filed on Dec. 6, 2011.

(51) Int. Cl.
| | |
|---|---|
| *C07H 21/02* | (2006.01) |
| *C07H 21/04* | (2006.01) |
| *A61K 31/70* | (2006.01) |
| *C12N 15/113* | (2010.01) |
| *A61K 31/713* | (2006.01) |
| *A61K 31/7105* | (2006.01) |
| *A61K 31/711* | (2006.01) |
| *A61K 49/04* | (2006.01) |
| *A61K 47/24* | (2006.01) |
| *A61K 9/00* | (2006.01) |
| *C12N 5/00* | (2006.01) |

(52) U.S. Cl.
CPC .......... *C12N 15/113* (2013.01); *A61K 9/0085* (2013.01); *A61K 31/711* (2013.01); *A61K 31/713* (2013.01); *A61K 31/7105* (2013.01); *A61K 47/24* (2013.01); *A61K 49/0438* (2013.01)

(58) Field of Classification Search
None
See application file for complete search history.

(56) References Cited

U.S. PATENT DOCUMENTS

| | | | |
|---|---|---|---|
| 5,447,711 A | 9/1995 | Almen et al. | |
| 8,679,460 B2 * | 3/2014 | Periasamy | A61K 49/0438 424/9.1 |
| 2003/0049203 A1 * | 3/2003 | Elmaleh | A61K 47/48007 424/1.73 |
| 2004/0152647 A1 * | 8/2004 | Reszka | A61K 9/1271 514/44 R |
| 2006/0182687 A1 * | 8/2006 | Yang | A61K 47/48092 424/9.364 |
| 2007/0248537 A1 * | 10/2007 | Yang | A61K 51/0491 424/1.49 |
| 2007/0292408 A1 * | 12/2007 | Singh | C12N 15/113 424/130.1 |
| 2010/0216238 A1 | 8/2010 | Baker et al. | |
| 2011/0077387 A1 * | 3/2011 | Hong | A61K 9/0085 536/23.2 |
| 2011/0085974 A1 * | 4/2011 | Chung | A61K 47/48069 424/1.65 |
| 2012/0322991 A1 * | 12/2012 | Montefeltro | A61K 47/48046 536/23.1 |

FOREIGN PATENT DOCUMENTS

| | | |
|---|---|---|
| WO | 2009048958 A2 | 4/2009 |
| WO | 2010148249 A1 | 12/2010 |
| WO | 2011112902 A2 | 9/2011 |

OTHER PUBLICATIONS

Alderson, Kathy. "Axonal swellings in human intramuscular nerves." Muscle & nerve 15.11 (1992): 1284-1289.
Andreassi, Catia, et al. "Aclarubicin treatment restores SMN levels to cells derived from type I spinal muscular atrophy patients." Human Molecular Genetics 10.24 (2001): 2841-2849.
Andreassi, Catia, et al. "Phenylbutyrate increases SMN expression in vitro: relevance for treatment of spinal muscular atrophy." European journal of human genetics 12.1 (2004): 59-65.
Arber, Silvia, et al. "Requirement for the homeobox gene Hb9 in the consolidation of motor neuron identity." Neuron 23.4 (1999): 659-674.
Avila, Amy M., et al. "Trichostatin A increases SMN expression and survival in a mouse model of spinal muscular atrophy." Journal of Clinical Investigation 117.3 (2007): 659-671.
Battle, D. J. et al. (2006). The Gemin5 protein of the SMN complex identifies snRNAs. Molecular cell, 23(2), 273-279.

(Continued)

*Primary Examiner* — Sean McGarry
(74) *Attorney, Agent, or Firm* — Meunier Carlin & Curfman LLC

(57) ABSTRACT

Disclosed are compositions comprising an antisense oligonucleotide and a non-ionic, low-osmolar contrast agent. Also disclosed are methods of delivering an antisense oligonucleotide to a target sire comprising incorporating the antisense oligonucleotide into a composition comprising a non-ionic, low-osmolar contrast agent. Also disclosed are methods of treating a neurodegenerative disease comprising administering one or more of the compositions disclosed herein.

10 Claims, 6 Drawing Sheets

(56) References Cited

OTHER PUBLICATIONS

Belteki, Gusztav, et al. "Conditional and inducible transgene expression in mice through the combinatorial use of Cre-mediated recombination and tetracycline induction." Nucleic acids research 33.5 (2005): e51-e51.
Azzouz, Mimoun, et al. "Lentivector-mediated SMN replacement in a mouse model of spinal muscular atrophy." Journal of Clinical Investigation 114.12 (2004): 1726-1731.
Boillée, Séverine, et al. "Onset and progression in inherited ALS determined by motor neurons and microglia." Science 312.5778 (2006): 1389-1392.
Burghes, A. H. (1997). When is a deletion not a deletion? When it is converted. American journal of human genetics, 61(1), 9-15.
Butchbach, Matthew ER, Jonathan D. Edwards, and Arthur HM Burghes. "Abnormal motor phenotype in the SMNΔ7 mouse model of spinal muscular atrophy." Neurobiology of disease 27.2 (2007): 207-219.
Butchbach, Matthew ER, et al. "A novel method for oral delivery of drug compounds to the neonatal SMNΔ7 mouse model of spinal muscular atrophy." Journal of neuroscience methods 161.2 (2007): 285-290.
Carnegie, G. K. et al. (2003). Protein phosphatase 4 interacts with the Survival of Motor Neurons complex and enhances the temporal localisation of snRNPs. Journal of cell science, 116(10), 1905-1913.
Carrel, T. L. et al. (2006). Survival motor neuron function in motor axons is independent of functions required for small nuclear ribonucleoprotein biogenesis. The Journal of neuroscience, 26(43), 11014-11022.
Cartegni, L., & Krainer, A. R. (2002). Disruption of an SF2/ASF-dependent exonic splicing enhancer in SMN2 causes spinal muscular atrophy in the absence of SMN1. Nature genetics, 30(4), 377-384.
Chang, Jan-Gowth, et al. "Treatment of spinal muscular atrophy by sodium butyrate." Proceedings of the National Academy of Sciences 98.17 (2001): 9808-9813.
Cheng, D. et al. (2007). The arginine methyltransferase CARM1 regulates the coupling of transcription and mRNA processing. Molecular cell, 25(1), 71-83.
Cifuentes-Diaz, Carmen, et al. "Deletion of murine SMN exon 7 directed to skeletal muscle leads to severe muscular dystrophy." The Journal of cell biology 152.5 (2001): 1107-1114.
Claus, P., Bruns, A., & Grothe, C. (2004). Fibroblast growth factor-223 binds directly to the survival of motoneuron protein and is associated with small nuclear RNAs. Biochem. J, 384, 559-565.
Coovert, D. D. et al. (1997). The survival motor neuron protein in spinal muscular atrophy. Human molecular genetics, 6(8), 1205-1214.
Cox, Gregory A., Connie L. Mahaffey, and Wayne N. Frankel. "Identification of the mouse neuromuscular degeneration gene and mapping of a second site suppressor allele." Neuron 21.6 (1998): 1327-1337.
Crawford, T. O., & Pardo, C. A. (1996). The neurobiology of childhood spinal muscular atrophy. Neurobiology of disease, 3(2), 97-110.
DiDonato, Christine J., et al. "Cloning, characterization, and copy number of the murine survival motor neuron gene: homolog of the spinal muscular atrophy-determining gene." Genome research 7.4 (1997): 339-352.
Dimos, John T., et al. "Induced pluripotent stem cells generated from patients with ALS can be differentiated into motor neurons." science 321.5893 (2008): 1218-1221.
Dodge, James C., et al. "Delivery of AAV-IGF-1 to the CNS extends survival in ALS mice through modification of aberrant glial cell activity." Molecular Therapy 16.6 (2008): 1056-1064.
Duque, Sandra, et al. "Intravenous administration of self-complementary AAV9 enables transgene delivery to adult motor neurons." Molecular Therapy 17.7 (2009): 1187-1196.
Echaniz-Laguna, A., Miniou, P., Bartholdi, D., & Melki, J. (1999). The promoters of the survival motor neuron gene (SMN) and its copy (SMNc) share common regulatory elements. The American Journal of Human Genetics, 64(5), 1365-1370.
Eggert, C., Chari, A., Laggerbauer, B., & Fischer, U. (2006). Spinal muscular atrophy: the RNP connection. Trends in molecular medicine, 12(3), 113-121.
Excoffon, Katherine JDA, et al. "Directed evolution of adeno-associated virus to an infectious respiratory virus." Proceedings of the National Academy of Sciences 106.10 (2009): 3865-3870.
Extended European Search Report and Written Opinion of the European Patent Office from Application No. EP 12855546.3, mailed Jul. 24, 2015, 5 pages.
Fan, L., & Simard, L. R. (2002). Survival motor neuron (SMN) protein: role in neurite outgrowth and neuromuscular maturation during neuronal differentiation and development. Human molecular genetics, 11(14), 1605-1614.
Feldkötter, M., Schwarzer, V., Wirth, R., Wienker, T. F., & Wirth, B. (2002). Quantitative analyses of SMN1 and SMN2 based on real-time lightCycler PCR: fast and highly reliable carrier testing and prediction of severity of spinal muscular atrophy. The American Journal of Human Genetics, 70(2), 358-368.
Forss-Petter, Sonja, et al. "Transgenic mice expressing β-galactosidase in mature neurons under neuron-specific enolase promoter control." Neuron 5.2 (1990): 187-197.
Foust, Kevin D., et al. "Intravascular AAV9 preferentially targets neonatal neurons and adult astrocytes." Nature biotechnology 27.1 (2009): 59-65.
Friesen, W. J. et al. (2001). The methylosome, a 20S complex containing JBP1 and pICln, produces dimethylarginine-modified Sm proteins. Molecular and cellular biology, 21(24), 8289-8300.
Frugier, Tony, et al. "Nuclear targeting defect of SMN lacking the C-terminus in a mouse model of spinal muscular atrophy." Human molecular genetics 9.5 (2000): 849-858.
Gabanella, Francesca, et al. "The activity of the spinal muscular atrophy protein is regulated during development and cellular differentiation." Human molecular genetics 14.23 (2005): 3629-3642.
Gabanella, Francesca, et al. "Ribonucleoprotein assembly defects correlate with spinal muscular atrophy severity and preferentially affect a subset of spliceosomal snRNPs." PloS one 2.9 (2007): e921-e921.
Gavrilina, Tatiana O., et al. "Neuronal SMN expression corrects spinal muscular atrophy in severe SMA mice while muscle-specific SMN expression has no phenotypic effect." Human molecular genetics 17.8 (2008): 1063-1075.
Gennarelli, M. et al. (1995). Survival motor-neuron gene transcript analysis in muscles from spinal muscular-atrophy patients. Biochemical and biophysical research communications, 213(1), 342-348.
Grimmler, Matthias, et al. "Phosphorylation regulates the activity of the SMN complex during assembly of spliceosomal U snRNPs." EMBO reports 6.1 (2005): 70-76.
Grimmler, Matthias, et al. "Unrip, a factor implicated in cap-independent translation, associates with the cytosolic SMN complex and influences its intracellular localization." Human molecular genetics 14.20 (2005): 3099-3111.
Gubitz, A. K., Feng, W., & Dreyfuss, G. (2004). The SMN complex. Experimental cell research, 296(1), 51-56.
Hahnen, E. et al. (1995). Molecular analysis of candidate genes on chromosome 5q13 in autosomal recessive spinal muscular atrophy: evidence of homozygous deletions of the SMN gene in unaffected individuals. Human Molecular Genetics, 4(10), 1927-1933.
Helmken, Claudia, et al. "Evidence for a modifying pathway in SMA discordant families: reduced SMN level decreases the amount of its interacting partners and Htra2-beta1." Human genetics 114.1 (2003): 11-21.
Hofmann, Y., Lorson, C. L., Stamm, S., Androphy, E. J., & Wirth, B. (2000). Htra2-β1 stimulates an exonic splicing enhancer and can restore full-length SMN expression to survival motor neuron 2 (SMN2). Proceedings of the National Academy of Sciences, 97(17), 9618-9623.
Hsieh-Li, Hsiu Mei, et al. "A mouse model for spinal muscular atrophy." Nature genetics 24.1 (2000): 66-70.

(56) References Cited

OTHER PUBLICATIONS

Huber, Andrea B., et al. "Distinct roles for secreted semaphorin signaling in spinal motor axon guidance." Neuron 48.6 (2005): 949-964.

International Search Report and Written Opinion of the International Searching Authority from Application No. PCT/US2012/068267, mailed May 7, 2013, 11 pages.

Jablonka, S., & Sendtner, M. (2003). Molecular and cellular basis of spinal muscular atrophy. Amyotrophic Lateral Sclerosis, 4(3), 144-149.

Jablonka, S. et al. (2007). Defective Ca2+ channel clustering in axon terminals disturbs excitability in motoneurons in spinal muscular atrophy. The Journal of cell biology, 179(1), 139-149.

Jarecki, Jill, et al. "Diverse small-molecule modulators of SMN expression found by high-throughput compound screening: early leads towards a therapeutic for spinal muscular atrophy." Human molecular genetics 14.14 (2005): 2003-2018.

Kashima, T. & Manley, J. L. (2003). A negative element in SMN2 exon 7 inhibits splicing in spinal muscular atrophy. Nature genetics, 34(4), 460-463.

Kaspar, Brian K., et al. "Retrograde viral delivery of IGF-1 prolongs survival in a mouse ALS model." Science 301.5634 (2003): 839-842.

Koerber, James T., Jae-Hyung Jang, and David V. Schaffer. "DNA shuffling of adeno-associated virus yields functionally diverse viral progeny." Molecular Therapy 16.10 (2008): 1703-1709.

Kolb, Stephen J., Daniel J. Battle, and Gideon Dreyfuss. "Molecular functions of the SMN complex." Journal of child neurology 22.8 (2007): 990-994.

Kong, Lingling, et al. "Impaired synaptic vesicle release and immaturity of neuromuscular junctions in spinal muscular atrophy mice." The Journal of Neuroscience 29.3 (2009): 842-851.

Le, Thanh T., et al. "SMNΔ7, the major product of the centromeric survival motor neuron (SMN2) gene, extends survival in mice with spinal muscular atrophy and associates with full-length SMN." Human molecular genetics 14.6 (2005): 845-857.

Lefebvre, S. et al. (1995). Identification and characterization of a spinal muscular atrophy-determining gene. Cell, 80(1), 155-165.

Lefebvre, S. et al. (1997). Correlation between severity and SMN protein level in spinal muscular atrophy. Nature genetics, 16(3), 265-269.

Liu, Q., & Dreyfuss, G. (1996). A novel nuclear structure containing the survival of motor neurons protein. The EMBO Journal, 15(14), 3555-3565.

Lorson, C. L. et al. (1998). SMN oligomerization defect correlates with spinal muscular atrophy severity. Nature genetics, 19(1), 63-66.

Lorson, C. L., Hahnen, E., Androphy, E. J., & Wirth, B. (1999). A single nucleotide in the SMN gene regulates splicing and is responsible for spinal muscular atrophy. Proceedings of the National Academy of Sciences, 96(11), 6307-6311.

Lorson, C. L., & Androphy, E. J. (2000). An exonic enhancer is required for inclusion of an essential exon in the SMA-determining gene SMN. Human molecular genetics, 9(2), 259-265.

Lueck, John D., et al. "Chloride channelopathy in myotonic dystrophy resulting from loss of posttranscriptional regulation for CLCN1." American Journal of Physiology-Cell Physiology 292.4 (2007): C1291-C1297.

Lunn, Mitchell R., et al. "Indoprofen upregulates the survival motor neuron protein through a cyclooxygenase-independent mechanism." Chemistry & biology 11.11 (2004): 1489-1493.

Maheshri, Narendra, et al. "Directed evolution of adeno-associated virus yields enhanced gene delivery vectors." Nature biotechnology 24.2 (2006): 198-204.

Mailman, M. D. et al. (2002). Molecular analysis of spinal muscular atrophy and modification of the phenotype by SMN2. Genetics in Medicine, 4(1), 20-26.

McAndrew, P. E. et al. (1997). Identification of proximal spinal muscular atrophy carriers and patients by analysis of SMN T and SMN C gene copy number. The American Journal of Human Genetics, 60(6), 1411-1422.

McWhorter, M. L., Monani, U. R., Burghes, A. H., & Beattie, C. E. (2003). Knockdown of the survival motor neuron (Smn) protein in zebrafish causes defects in motor axon outgrowth and pathfinding. The Journal of cell biology, 162(5), 919-932.

McWhorter, Michelle L., et al. "The SMN binding protein Gemin2 is not involved in motor axon outgrowth." Developmental neurobiology 68.2 (2008): 182-194.

Meister, G. et al. (2000). Characterization of a nuclear 20S complex containing the survival of motor neurons (SMN) protein and a specific subset of spliceosomal Sm proteins. Human molecular genetics, 9(13), 1977-1986.

Meister, G. et al. (2001). Methylation of Sm proteins by a complex containing PRMT5 and the putative U snRNP assembly factor pICln. Current Biology, 11(24), 1990-1994.

Melki, J. (1997). Spinal muscular atrophy. Current opinion in neurology, 10(5), 381-385.

Monani, U. R. et al. (1999). A single nucleotide difference that alters splicing patterns distinguishes the SMA gene SMN1 from the copy gene SMN2. Human molecular genetics, 8(7), 1177-1183.

Monani, U. R., McPherson, J. D., & Burghes, A. H. (1999). Promoter analysis of the human centromeric and telomeric survival motor neuron genes (SMN C and SMN T). Biochimica et Biophysica Acta (BBA)-Gene Structure and Expression, 1445(3), 330-336.

Monani, Umrao R., et al. "The human centromeric survival motor neuron gene (SMN2) rescues embryonic lethality in Smn-/-mice and results in a mouse with spinal muscular atrophy." Human molecular genetics 9.3 (2000): 333-339.

Monani, Umrao R., et al. "A transgene carrying an A2G missense mutation in the SMN gene modulates phenotypic severity in mice with severe (type I) spinal muscular atrophy." The Journal of cell biology 160.1 (2003): 41-52.

Narayanan, U. et al. (2002). SMN, the spinal muscular atrophy protein, forms a pre-import snRNP complex with snurportin1 and importin β. Human molecular genetics, 11(15), 1785-1795.

Novoyatleva, Tatyana, et al. "Protein phosphatase 1 binds to the RNA recognition motif of several splicing factors and regulates alternative pre-mRNA processing." Human molecular genetics 17.1 (2008): 52-70.

Ogawa, Chihiro, et al. "Gemin2 plays an important role in stabilizing the survival of motor neuron complex." Journal of Biological Chemistry 282.15 (2007): 11122-11134.

Oprea, G. E. et al. (2008). Plastin 3 is a protective modifier of autosomal recessive spinal muscular atrophy. Science, 320(5875), 524-527.

Pasinelli, Piera, and Robert H. Brown. "Molecular biology of amyotrophic lateral sclerosis: insights from genetics." Nature Reviews Neuroscience 7.9 (2006): 710-723.

Pearn, J. O. H. N. (1978). Incidence, prevalence, and gene frequency studies of chronic childhood spinal muscular atrophy. Journal of Medical Genetics, 15(6), 409-413.

Pellizzoni, L., Yong, J., & Dreyfuss, G. (2002). Essential role for the SMN complex in the specificity of snRNP assembly. Science, 298(5599), 1775-1779.

Roberts, D. F., & Chavez, J. (1970). The genetic component in child mortality. Archives of disease in childhood, 45(239), 33-38.

Rossoll, W. et al. (2002). Specific interaction of Smn, the spinal muscular atrophy determining gene product, with hnRNP-R and gry-rbp/hnRNP-Q: a role for Smn in RNA processing in motor axons? Human molecular genetics, 11(1), 93-105.

Rossoll, W. et al. (2003). Smn, the spinal muscular atrophy-determining gene product, modulates axon growth and localization of β-actin mRNA in growth cones of motoneurons. The Journal of cell biology, 163(4), 801-812.

Sargeant, Aaron M., et al. "OSU-HDAC42, a histone deacetylase inhibitor, blocks prostate tumor progression in the transgenic adenocarcinoma of the mouse prostate model." Cancer research 68.10 (2008): 3999-4009.

(56) References Cited

OTHER PUBLICATIONS

Schrank, B. et al. (1997). Inactivation of the survival motor neuron gene, a candidate gene for human spinal muscular atrophy, leads to massive cell death in early mouse embryos. Proceedings of the National Academy of Sciences, 94(18), 9920-9925.
Sendtner, Michael, Georg W. Kreutzberg, and Hans Thoenen. "Ciliary neurotrophic factor (CNTF) prevents the degeneration of motor neurons after axotomy." Nature (1990) 345, 6274, 440-441.
Setola, V. et al. (2007). Axonal-SMN (a-SMN), a protein isoform of the survival motor neuron gene, is specifically involved in axonogenesis. Proceedings of the National Academy of Sciences, 104(6), 1959-1964.
Sharma, A. et al. (2005). A role for complexes of survival of motor neurons (SMN) protein with gemins and profilin in neurite-like cytoplasmic extensions of cultured nerve cells. Experimental cell research, 309(1), 185-197.
Sheth, Nihar, et al. "Comprehensive splice-site analysis using comparative genomics." Nucleic acids research 34.14 (2006): 3955-3967.
Shpargel, Karl B., and A. Gregory Matera. "Gemin proteins are required for efficient assembly of Sm-class ribonucleoproteins." Proceedings of the National Academy of Sciences of the United States of America 102.48 (2005): 17372-17377.
Swoboda, K. J. et al. (2005). Natural history of denervation in SMA: relation to age, SMN2 copy number, and function. Annals of neurology, 57(5), 704-712.
Sumner, Charlotte J., et al. "Valproic acid increases SMN levels in spinal muscular atrophy patient cells." Annals of neurology 54.5 (2003): 647-654.
Sumner, C. J. et al. (2006). SMN mRNA and protein levels in peripheral blood Biomarkers for SMA clinical trials. Neurology, 66(7), 1067-1073.
Tarrade, Anne, et al. "A mutation of spastin is responsible for swellings and impairment of transport in a region of axon characterized by changes in microtubule composition." Human molecular genetics 15.24 (2006): 3544-3558.
Thaler, Joshua, et al. "Active suppression of interneuron programs within developing motor neurons revealed by analysis of homeodomain factor HB9." Neuron 23.4 (1999): 675-687.
Thurmond, John, et al. "Synthesis and biological evaluation of novel 2, 4-diaminoquinazoline derivatives as SMN2 promoter activators for the potential treatment of spinal muscular atrophy." Journal of medicinal chemistry 51.3 (2008): 449-469.
Ule, Jernej, et al. "An RNA map predicting Nova-dependent splicing regulation." Nature 444.7119 (2006): 580-586.
Vezain, Myriam, et al. "A sensitive assay for measuring SMN mRNA levels in peripheral blood and in muscle samples of patients affected with spinal muscular atrophy." European Journal of Human Genetics 15.10 (2007): 1054-1062.
Vitte, Jérémie M., et al. "Deletion of murine Smn exon 7 directed to liver leads to severe defect of liver development associated with iron overload." The American journal of pathology 165.5 (2004): 1731-1741.
Viollet, Louis, et al. "cDNA isolation, expression, and chromosomal localization of the mouse survival motor neuron gene (Smn)." Genomics 40.1 (1997): 185-188.
Wan, Lili, et al. "The survival of motor neurons protein determines the capacity for snRNP assembly: biochemical deficiency in spinal muscular atrophy." Molecular and cellular biology 25.13 (2005): 5543-5551.
Wichterle, Hynek, et al. "Directed differentiation of embryonic stem cells into motor neurons." Cell 110.3 (2002): 385-397.
Will, C. L. et al. (2001). A novel U2 and U11/U12 snRNP protein that associates with the pre-mRNA branch site. The EMBO journal, 20(16), 4536-4546.
Winkler, Christoph, et al. "Reduced U snRNP assembly causes motor axon degeneration in an animal model for spinal muscular atrophy." Genes & development 19.19 (2005): 2320-2330.
Yamanaka, Koji, et al. "Astrocytes as determinants of disease progression in inherited amyotrophic lateral sclerosis." Nature neuroscience 11.3 (2008): 251-253.
Young, P. J. et al. (2000). The relationship between SMN, the spinal muscular atrophy protein, and nuclear coiled bodies in differentiated tissues and cultured cells. Experimental cell research, 256(2), 365-374.
Young, P. J. et al. (2001). Nuclear gems and Cajal (coiled) bodies in fetal tissues: nucleolar distribution of the spinal muscular atrophy protein, SMN. Experimental cell research, 265(2), 252-261.
Zerres, K., & Rudnik-Schöneborn, S. (1995). Natural history in proximal spinal muscular atrophy: clinical analysis of 445 patients and suggestions for a modification of existing classifications. Archives of neurology, 52(5), 518-523.
Zhang, H. Z., et al. "A proteolytic transmembrane signaling pathway and resistance to β-lactams in *Staphylococci*." Science 291. 5510 (2001): 1962-1965.
Zhang, H. L. et al. (2003). Active transport of the survival motor neuron protein and the role of exon-7 in cytoplasmic localization. The Journal of neuroscience, 23(16), 6627-6637.
Zhang, H. et al. (2006). Multiprotein complexes of the survival of motor neuron protein SMN with Gemins traffic to neuronal processes and growth cones of motor neurons. The Journal of neuroscience, 26(33), 8622-8632.
Zhang, Zhenxi, et al. "SMN deficiency causes tissue-specific perturbations in the repertoire of snRNAs and widespread defects in splicing." Cell 133.4 (2008): 585-600.
Examination Report No. 1 issued in Australian Application No. 2012347765, dated Dec. 6, 2016.

\* cited by examiner

SEQUENCE LISTING

```
<160> NUMBER OF SEQ ID NOS: 16

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
ttaaggagta agtctgccag cattatgaaa agtgaatgtt                              40

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
gtaaaatgtc ttgtgaaaca aaatgctttt taacatccat ataaa                        45

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
ttttacaaaa gtaagattca ctttcataat gctggcagac ttactcctta a                 51

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence; note =
      synthetic construct
```

```
<400> SEQUENCE: 4
tttatatgga tgttaaaaag cattttgttt cacaagacat tttac                    45

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
attcactttc ataatgctg                                                 19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
attcactttc ataatgctgg                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 7
tcctttaaag tattgtgacc                                                20

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8
ttatatactt ttaaacatat agaagatag                                      29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 9
agattctctt gatgatgctg aatg                                           24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct
```

```
<400> SEQUENCE: 10
gtttcagaca aaatcaaaaa gaagga                                          26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
tctataacgc ttcacattcc agatct                                          26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12
atgccagcat ttctccttaa tttaagg                                         27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 13
gtcaacccca ccgtgttctt                                                 20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 14
ttggaacttt gtctgcaaac a                                               21

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 15
cttgggccgc gtct                                                       14

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 16
cctcttacct cagttacaat ttata                                           25
```

NON-IONIC, LOW OSMOLAR CONTRAST AGENTS FOR DELIVERY OF ANTISENSE OLIGONUCLEOTIDES AND TREATMENT OF DISEASE

CROSS-REFERENCE TO RELATED APPLICATIONS

This application is a National Phase Application of International Application No. PCT/US2012/068267, filed Dec. 6, 2012, which claims priority to U.S. Provisional Application No. 61/567,416, filed Dec. 6, 2011, both of which are incorporated herein fully by reference.

This work was supported by the National Institutes of Health grants R01 HD060586 and RC2 NS069476. The United States government has certain rights in the invention.

BACKGROUND

Large-molecule drugs do not cross the blood-brain-barrier (BBB) and 98% of small-molecules cannot penetrate this barrier, thereby limiting drug development efforts for many CNS disorders Gene delivery has recently been proposed as a method to bypass the BBB; however, widespread delivery to the brain and spinal cord has been challenging. The development of successful gene therapies for motor neuron disease will likely require widespread transduction within the spinal cord and motor cortex. Two of the most common motor neuron diseases are spinal muscular atrophy (SMA) and amyotrophic lateral sclerosis (ALS), both debilitating disorders of children and adults, respectively, with no effective therapies to date. Recent work in rodent models of SMA and ALS involves gene delivery using viruses that are retrogradely transported following intramuscular injection. However, clinical development may be difficult given the numerous injections required to target the widespread region of neurodegeneration throughout the spinal cord, brainstem and motor cortex to effectively treat these diseases. Moreover, the problem of lack of wide spread distribution of a genetic based therapy in a tissue, organ, or system extends beyond merely neurological conditions. What is needed are methods and compositions for delivering genetic based therapies to target sites in a widespread region that is affected by a disease.

SUMMARY

Disclosed are methods and compositions related to achieving whole system delivery of antisense oligonucleotides.

In one aspect, disclosed herein are compositions comprising an antisense oligonucleotide and a non-ionic, low-osmolar contrast agent. It is understood and herein contemplated that the antisense oligonucleotide can comprise a morpholino, an siRNA, or an shRNA. It is further contemplated that the low-osmolar contrast agent can comprise iobitridol, iohexyl, iomeprol, iopamidol, iopentol, iopromide, ioversol or ioxilan.

In one aspect, also disclosed are methods of delivering an antisense oligonucleotide to any target tissue or throughout a system comprising administering the antisense oligonucleotide in the form of a composition further comprising a non-ionic, low-osmolar contrast agent. It is understood and herein contemplated that the antisense oligonucleotide can comprise a morpholino, an siRNA, or an shRNA. It is further contemplated that the low-osmolar contrast agent can comprise iobitridol, iohexyl, iomeprol, iopamidol, iopentol, iopromide, ioversol or ioxilan.

Also disclosed are methods of treating a neurodegenerative disorder in a subject comprising administering to the subject one or more of the compositions disclosed herein.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 2 shows Survival curves of mice treated with ASOs.

FIG. 3 shows Analysis of exon 7 incorporation by SMN2 transcript.

FIG. 4 shows incorporation and survival of E1 in mice.

DETAILED DESCRIPTION

Figure 1:
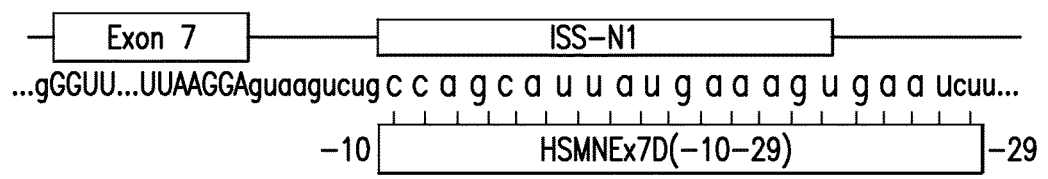
FIG. 1 shows an illustration of SMN2 exon and intron 7 with highlighted ISS-N1 (including SEQ ID NO: 1) and the target site for morpholino HSMNEx7D(−10-29) (MO).

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods of Performing Widespread Delivery of a Composition

It is contemplated herein that the use of a non-ionic, low-osmolar contrast agent will enable an anti-sense oligonucleotide to cross the blood-brain-barrier and to be delivered to any tissue throughout the body of a subject and in particular throughout the entire nervous system including the central nervous system and peripheral nervous system. In one aspect, disclosed herein are methods of delivering an antisense oligonucleotide (ASO) to a tissue in a subject comprising administering to the subject a composition comprising an antisense oligonucleotide and a non-ionic, low-osmolar contrast agent to the subject. The non-ionic, low-osmolar contrast agent, such as, for example, iohexyl, can move the morpholino across the blood brain barrier and increase distribution throughout tissue. For example, the non-ionic, low-osmolar contrast agent can deliver the anti-sense oligonucleotide to the central nervous system, peripheral nervous system, autonomic nervous system, brain, spinal cord, cardiac muscle, skeletal muscle, liver, pancreas, prostate, eyes, kidneys, small intestines, large intestines, stomach, spleen, thymus, pituitary gland, thyroid gland, bone marrow, bone, cartilage, or cancerous tissue. Thus, also disclosed herein are methods of delivering an ASO wherein the ASO is delivered to the central nervous system, peripheral nervous system, autonomic nervous system, brain, spinal cord, cardiac muscle, skeletal muscle, liver, pancreas, prostate, eyes, kidneys, small intestines, large intestines, stomach, spleen, thymus, pituitary gland, thyroid gland, bone marrow, bone, cartilage, of the subject or cancerous tissue in the subject. In one aspect, it is disclosed herein that the ASO is delivered to the central nervous system of a subject. For example, the ASO can be delivered to the brain, the spinal cord, a glial cell, an astrocyte, or a lower motor neuron.

It is contemplated herein that the use of a non-ionic, low-osmolar contrast agent will enable an anti-sense oligonucleotide to cross the blood-brain-barrier and to be delivered to any tissue throughout the body of a subject and in particular throughout the entire nervous system including the central nervous system and peripheral nervous system. In one aspect, disclosed herein are methods of delivering an antisense oligonucleotide (ASO) to a tissue in a subject comprising administering to the subject a composition comprising an antisense oligonucleotide and a non-ionic, low-osmolar contrast agent to the subject. For example, the non-ionic, low-osmolar contrast agent can deliver the anti-sense oligonucleotide to the central nervous system, peripheral nervous system, autonomic nervous system, brain, spinal cord, cardiac muscle, skeletal muscle, liver, pancreas, prostate, eyes, kidneys, small intestines, large intestines, stomach, spleen, thymus, pituitary gland, thyroid gland, bone marrow, bone, cartilage, or cancerous tissue. Thus, also disclosed herein are methods of delivering an ASO wherein the ASO is delivered to the central nervous system, peripheral nervous system, autonomic nervous system, brain, spinal cord, cardiac muscle, skeletal muscle, liver, pancreas, prostate, eyes, kidneys, small intestines, large intestines, stomach, spleen, thymus, pituitary gland, thyroid gland, bone marrow, bone, cartilage, of the subject or cancerous tissue in the subject. In one aspect, it is disclosed herein that the ASO is delivered to the central nervous system of a subject. For example, the ASO can be delivered to the brain, the spinal cord, a glial cell, an astrocyte, or a lower motor neuron.

To efficiently and exhaustively distribute the ASO throughout a tissue, organ system or body or to increase delivery of the ASO, the ASO can be administered in a composition further comprising a non-ionic, low-osmolar contrast agent. Examples of non-ionic, low-osmolar contrast agents include, but are not limited to iobitridol, iohexyl, iomeprol, iopamidol, iopentol, iopromide, ioversol or ioxilan. Accordingly, in one aspect, disclosed herein are methods of delivering an antisense oligonucleotide (ASO) to a tissue in a subject comprising administering to the subject a composition comprising an antisense oligonucleotide and a non-ionic, low-osmolar contrast agent to the subject, wherein the non-ionic, low-osmolar contrast agent is iohexyl. In another aspect, disclosed herein are methods of improving the distribution of an ASO comprising admixing and ASO with a non-ionic, low-osmolar contrast agent.

Examples ASO are well-known in the art and include but are not limited to shRNA, siRNA, and morpholinos. In one aspect, the disclosed ASO (e.g., morpholinos) can bind to a survival motor neuron (SMN) gene, a mutated SOD1 gene, C9orf72 repeats, DMPK repeats, ZNF9 repeats, alpha-synuclein, or a negative regulatory element in intron 6 or intron 7 of SMN2. For example, the ASO can be a morpholino that binds CAG repeats, CTG repeats, CCTG repeats, or GGGCC repeats. In one aspect the ASO can comprise a morpholino that binds SMN2 between nucleotides 67 and 112, upstream of exon 7 (E1) (GTAAAAT- GTCTTGTGAAACAAAATGCTTTTTAACATC-
CATATAAA SEQ ID NO: 2) or SMN2 10 nucleotides
downstream of exon 7 (intronic splicing silencer N1 (ISS-
N1)(see SEQ ID NO: 1 TTAAGGAGTAAGTCTGCCAG-
CATTATGAAAAGTGAATGTT) or any fragment of either
at least 15 nucleotides in length. For example, the ASO can
be a morpholino comprising at least 15 contiguous nucleic
acids as disclosed in SEQ ID NO: 3 (5'-TTTTACAAAAG-
TAAGATTCACTTTCATAATGCTGGCAGACTTACTC-
CTTAA-3') or SEQ ID NO: 4 (TTTATATGGATGT-
TAAAAAGCATTTTGTTTCACAAGACATTTTAC). In
another aspect, the ASO can be a morpholino comprising the
sequence ATTCACTTTCATAATGCTG (SEQ ID NO: 5),
ATTCACTTTCATAATGCTGG (SEQ ID NO: 6), or
TCCTTTAAAGTATTGTGACC (SEQ ID NO: 7).

C. Compositions

Disclosed are the components to be used to prepare the
disclosed compositions as well as the compositions themselves to be used within the methods disclosed herein. These
and other materials are disclosed herein, and it is understood
that when combinations, subsets, interactions, groups, etc. of
these materials are disclosed that while specific reference of
each various individual and collective combinations and
permutation of these compounds may not be explicitly
disclosed, each is specifically contemplated and described
herein. For example, if a particular antisense oligonucleotide
is disclosed and discussed and a number of modifications
that can be made to a number of molecules including the
antisense oligonucleotide are discussed, specifically contemplated is each and every combination and permutation of
the antisense oligonucleotide and the modifications that are
possible unless specifically indicated to the contrary. Thus,
if a class of molecules A, B, and C are disclosed as well as
a class of molecules D, E, and F and an example of a
combination molecule, A-D is disclosed, then even if each is
not individually recited each is individually and collectively
contemplated meaning combinations, A-E, A-F, B-D, B-E,
B-F, C-D, C-E, and C-F are considered disclosed. Likewise,
any subset or combination of these is also disclosed. Thus,
for example, the sub-group of A-E, B-F, and C-E would be
considered disclosed. This concept applies to all aspects of
this application including, but not limited to, steps in methods of making and using the disclosed compositions. Thus,
if there are a variety of additional steps that can be performed it is understood that each of these additional steps
can be performed with any specific embodiment or combination of embodiments of the disclosed methods.

In one aspect, disclosed herein are compositions comprising an antisense oligonucleotide and a non-ionic, low-osmolar contrast agent.

1. Non-ionic, Low-Osmolar Contrast Agent

As disclosed herein non-ionic, low-osmolar contrast agent
refers to any non-ionic, low-osmolar substance used to
enhance the contrast of structures or fluids within the body
in medical imaging. It is understood and herein contemplated that non-ionic, low-osmolar contrast agents bind to a
target tissue or other molecule through hydrogen bonds
between the contrast agent and the charged surface of the
proteins on the surface of the tissue or to another nucleic
acid, amino acid, peptide, or protein. Such agents include
but are not limited to iobitridol, iohexyl, iomeprol, iopamidol, iopentol, iopromide, ioversol or ioxilan. Thus, for
example, disclosed herein are compositions comprising an
ASO and a non-ionic, low-osmolar contrast agent, wherein
the non-ionic, low-osmolar contrast agent comprises
iohexyl.

2. Antisense Oligonucleotides

Examples ASO are well-known in the art and include but
are not limited to shRNA, siRNa, and morpholinos. Thus, in
one aspect disclosed herein are compositions comprising a
shRNA, siRNA, or morpholino and a non-ionic, low-osmolar contrast agent. In one aspect, the antisense oligonucleotides have a neutral charge yet surprising retain an ability
to sequester and be bound by the non-ionic, low-osmolar
contrast agents disclosed herein. The ASO morpholino or
other chemistry is administered to block specific splicing
events either encouraging incorporation of an exon (s) in a
transcript or removing an exon(s) or blocking of a repeat
transcript from accumulation of RNA binding proteins. Thus
a transcript can be blocked from making a toxic protein or
enhanced in making a beneficial protein or blocking of RNA
accumulating RNA binding proteins inappropriately. Non-ionic, low-osmolar contrast agents improve distribution of
morpholino to organs and tissues.

Thus, in one aspect, the disclosed ASO (e.g., morpholinos) can bind to a survival motor neuron (SMN) gene, a
mutated SOD1 gene, C9orf72 repeats, DMPK repeats,
ZNF9 repeats, alpha-synuclein, or a negative regulatory
element in intron 6 or intron 7 of SMN2. For example, the
ASO can be a morpholino that binds CAG repeats, CTG
repeats, CCTG repeats, or GGGCC repeats. It is understood
and herein contemplated that ASO can effect transcription
and/or translation by binding to the surface of a nucleic acid.
Once bound, an ASO can disrupt translation, bind to a target
nucleotide, induce exon skipping, block an intron splice
silencer, block an exon splice enhancer, bind to a repeat
nucleotide sequence, or block binding to a sequence in toxic
RNA. In some embodiments, vectors encode short hairpin
RNAs directed at mutated proteins such as superoxide
dismutase for ALS, or neurotropic factors such as GDNF or
IGF1 for ALS, Rett's Syndrome, or Parkinson's disease.

3. Morpholinos

Herein, "morpholino" refers to neutrally charged synthetic oligonucleotides which have standard nucleic acid
bases, bound to morpholino rings rather than the deoxyribose rings of DNA and the bases are linked through phosphorodiamidate groups instead of phosphates. The morpholino operates by binding to complementary RNA and
blocks access to the RNA by other molecules. Disclosed
herein, the morpholino may also be used to displace a
molecule that is already bound to the complementary RNA
strand.

In one aspect the ASO can comprise a morpholino that
binds SMN2 between nucleotides 67 and 112, upstream of
exon 7 (E1) (GTAAAATGTCTTGTGAAACAAAAT-
GCTTTTTAACATCCATATAAA SEQ ID NO: 2) or SMN2
10 nucleotides downstream of exon 7 (intronic splicing
silencer N1 (ISS-N1)(see SEQ ID NO: 1 TTAAGGAG-
TAAGTCTGCCAGCATTATGAAAAGTGAATGTT) or
any fragment of either at least 15 nucleotides in length. For
example, the ASO can be a morpholino comprising at least
15 contiguous nucleic acids as disclosed in SEQ ID NO: 3
(5'-TTTTACAAAAGTAAGATTCACTTTCATAATGCTG-
GCAGACTTACTCCTTAA-3') or SEQ ID NO: 4 (TT-
TATATGGATGTTAAAAAGCATTTTGTTTCACAAGA-
CATTTTAC). In another aspect, the ASO can be a
morpholino comprising the sequence
ATTCACTTTCATAATGCTG (SEQ ID NO: 5),
ATTCACTTTCATAATGCTGG (SEQ ID NO: 6), or
TCCTTTAAAGTATTGTGACC (SEQ ID NO: 7).

Disclosed herein, administration of a single morpholino
ASO resulted in an increase in survival from 14 days to over
100 days in delta7 SMA mice when delivered by ICV. This is a dramatic improvement compared to morpholino ASO administration which gives an increase in survival to just 20-25 days. Furthermore, the morpholinos have shown no toxicity even at high doses whereas 8 µg/g of MOE ASO has demonstrated toxicity when given by ICV into neonatal mice. Thus the disclosed ASO morpholino composition is a viable option for treatment of SMA in humans.

Morpholino (MO) ASOs have been used in various studies for alteration of genes. Probably the most common use of morpholino ASOs is in the modification of zebrafish genes where delivery to embryos is rapid, efficient, and has limited toxicity. Furthermore, morpholinos have been used to modify the splicing of the Dystrophin gene. Morpholinos have been used to induce exon skipping to create an in-frame transcript, thus restoring Dystrophin expression in Duchenne Muscular Dystrophy. Two types of antisense oligonucleotide chemistries have been investigated: 2'O Me phosphorothiate RNA (Prosensa) and morpholino (Sarepta Therapeutics, formerly AVI). The morpholino skipping ASOs have been used in trials of Duchene patients and have shown induction of Dystrophin in patients with low toxicity in preclinical testing. At higher doses these morpholinos have also shown efficacy in the six-minute walk test.

The disclosed compositions can comprise morpholino (MO) antisense oligonucleotides (ASOs) complexed with Iohexyl. The morpholino is viewed by the FDA in the U.S. as a distinct chemical entity. This is also true of the Dystrophin skipping oligonucleotides which have been tested and are considered separate entities. When compared to MOE this situation is much like having two drug compounds (MOE and morpholino) to the same target receptor (ISS-N1 in this case). The E1 MO ASO is directed against a separate target, but both ISS-N1 and E1 MOs result in an increased incorporation of SMN exon 7 into SMN2.

The mode of action of the composition, as shown in the examples, is by binding sequences within the SMN2 gene that enhance incorporation of exon 7 into the transcript, thus increasing the amount of SMN produced by SMN2. Therefore, the composition can be administered to the animal at a time when increasing SMN has an effect. In the delta7 mouse model, the greatest benefit can be achieved with administration prior to PND6. Interestingly, EMG studies in the delta7 model indicate the large drop in motor unit number estimation (MUNE) numbers comes between PND6 and PND8 days. For SMA Type 1 treatments, it can be preferable to administer the morpholino composition prior to the motor neuron drop as identified by MUNE. It is also interesting to note that even in Type 2 SMA, the MUNE studies indicate a drop within the early phase of the disease that is complete by the age of 2. Thus it likely that motor neurons drop out early but to a different level in each type of SMA. The progression can then be due to loss of motor neurons with aging as well as the heavy work load the remaining motor neurons must endure. It is hard to know how SMN levels influence this process, but it can be noted that in mice, removal of high levels of SMN in a mouse after correction of the SMA phenotype does not have a major impact on the neuromuscular system. Thus the requirement for high SMN levels later in life is debatable.

As shown in the Examples herein, the morpholino composition bioactivity in the delta7 mouse models has been shown that a single ICV dose gives an increase in survival from 14 days to over 100 days.

4. Homology/Identity

It is understood that one way to define any known variants and derivatives or those that might arise, of the disclosed genes herein is through defining the variants and derivatives in terms of homology to specific known sequences. For example SEQ ID NO: 3 sets forth a particular sequence of a morpholino. Specifically disclosed are variants of these and other genes disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

5. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

6. Nucleic Acids

There are a variety of molecules disclosed herein that are nucleic acid based, including for example the nucleic acids that encode, for example the ISS-N1 morpholino, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, *Antisense Research and Applications, pages* 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modifcation, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. 2' sugar modiifcations also include but are not limited to —O[$(CH_2)_n$O]$_m$CH$_3$, —O$(CH_2)_n$OCH$_3$, —O$(CH_2)_n$NH$_2$, —O$(CH_2)_n$CH$_3$, —O$(CH_2)_n$—ONH$_2$, and —O$(CH_2)_n$ON[$(CH_2)_n$CH$_3$]$_2$, where n and m are from 1 to about 10.

Other modifications at the 2' position include but are not limted to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-5-tritylthiol (Manoharan et al., Ann. N.Y. Acad. Sci., 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylaminocarbonyl-oxycholesterol moiety (Crooke et al., *J. Pharmacol. Exp. Ther.,* 1996, 277, 923-937.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

a) Sequences

There are a variety of sequences related to any of the nucleic acids disclosed herein all of which are encoded by nucleic acids or are nucleic acids. The sequences for the human analogs of these genes, as well as other analogs, and alleles of these genes, and splice variants and other types of variants, are available in a variety of gene databases, including Genbank. Those of skill in the art understand how to resolve sequence discrepancies and differences and to adjust the compositions and methods relating to a particular sequence to other related sequences. Primers and/or probes can be designed for any given sequence given the information disclosed herein and known in the art.

b) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule. It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate.

7. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

As used herein, the terms "administering" and "administration" refer to any method of providing a pharmaceutical preparation to a subject. The compositions may be administered orally, parenterally (e.g., intravenously), by intramuscular injection, by intraperitoneal injection, intrathecally, intracerebrally, by intracerberal ventricular injection, transdermally, extracorporeally, subcutaneously, topically or the like, including topical intranasal administration or administration by inhalant. As used herein, it is understood that ICV is a method that bypasses the blood-brain barrier (BBB) and other mechanisms that limit pharmaceutical preparation distribution into the CNS by introducing the composition directly into the ventricles of the brain. This route of administration allows for high concentrations of an administered composition in the central compartment, and can be an effective route of administration for administering compositions that act on the CNS but may be unable to cross the BBB.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. In one aspect, the disclosed ASO and contrast agent containing compositions can be administered intrathecally to the brain, spinal cord, glial cells, astrocytes, or lower motor neurons to deliver the ASO to a tissue or to treat a neurodegenerative disease as disclosed herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Administration can additionally comprise the use of pumps. Pumps, including, but not limited to, peristaltic pumps, infusion pumps, and syringe pumps can be used to enable continuous or intermittent administration of a composition for a specified period of time. For example, a composition comprising an ASO and iohexyl can be administered by via a pump directly into the CNS of a patient over a period of time determined by those of skill in the art.

Administration can additionally comprise the use of ports. Ports are medical devices used to reduce punctures when administering a pharmaceutical composition through the skin. A port provides access to an area of administration via a cannula, and ports can be set up to receive syringes or tubing systems. For example, a port may be applied to a subject to provide access to the subject's CNS such that multiple administrations of a composition comprising an ASO and iohexyl can be injected through the same port. Alternatively, a port may be applied to a subject to provide access to the subject's CNS such that a pump can be attached to the port for continuous administration of a composition comprising an ASO and iohexyl.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as a morpholino, for treating, inhibiting, or preventing an SMA, the efficacy of the therapeutic morpholino can be assessed in various ways well known to the skilled practitioner. For instance, one of ordinary skill in the art will understand that a composition, such as a morpholino, disclosed herein is efficacious in treating or inhibiting SMA in a subject by observing that the composition rescued the non disease state through the use of survival studies such as those utilizing the SNA delta7 mice described herein.

8. Compositions with Similar Functions

It is understood that the compositions disclosed herein have certain functions, such as, for example binding SMN2 or binding CAG, CTG, CCTG, GGGGCC repeats as well as repeats associated with DMPK, ZNF9, and C9orf72 genes that result in a disease state. Disclosed herein are certain structural requirements for performing the disclosed functions, and it is understood that there are a variety of structures which can perform the same function which are related to the disclosed structures, and that these structures will ultimately achieve the same result.

D. Methods Of Making The Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

E. Methods Of Treating A Neurodegenerative Disorder

"Treatment," "treat," or "treating" mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of SMA is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. Nevertheless, it is fully contemplated herein that "treatment" can not only refer to the ablation of the disease state, but the reversal of the condition.

In one aspect, the ASO and contrast agent containing compositions disclosed herein can be used to treat neurodegenerative disease. In one aspect, the disclosed treatment methods can be used to treat any neurodegenerative disease, including but not limited to Alzheimer's disease, Spinal muscular atrophy (SMA), Myotonic dystrophy, Huntington's disease, Spinocerebellar degeneration, Rett Syndrome, Spinocerebellar ataxia, Friedreich's ataxia, Ataxia telangiectasia, Charcot-Marie-Tooth disease, Vasomotor ataxia, Vestibulocerebellar, Ataxiadynamia, Ataxiophemia, Amyotrophic lateral sclerosis, and Olivopontocerebellar atrophy as well as Pompe disease, lysosomal storage disorders, Glioblastoma multiforme and Parkinson's disease. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), 1-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis 1/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis, Infantile, Sandhoff Disease/GM2 gangliosidosis, Juvenile, Schindler disease, Salla disease/Sialic Acid Storage Disease, Tay-Sachs/GM2 gangliosidosis, and Wolman disease. Thus, for example, disclosed herein are methods of treating a neurodegenerative disease in a patient in need thereof comprising intrathecal delivery of a morpholino and a non-ionic, low-osmolar contrast agent to the patient.

In one aspect the neurodegenerative disease can be selected from the group consisting of Alzheimer's disease, spinal muscular atrophy (SMA), Myotonic dystrophy, Huntington's disease, Parkinson's disease, amyotrophic lateral sclerosis, Spinocerebellar degeneration, Spinocerebellar ataxia, Friedreich's ataxia, Ataxia telangiectasia, Charcot-Marie-Tooth disease, Vasomotor ataxia, Vestibulocerebellar, Ataxiadynamia, Ataxiophemia, Amyotrophic lateral sclerosis, and Olivopontocerebellar atrophy.

Spinal muscular atrophy (SMA). SMA is an autosomal recessive disorder caused by loss or mutation of the SMN1 gene and retention of SMN2 which leads to insufficient levels of SMN protein in motor neurons. In the most severe cases of the disease, paralysis leads to respiratory failure and death usually by two years of age. SMA is the second most common pediatric autosomal recessive disorder behind cystic fibrosis with an incidence of 1 in 6000 live births. SMA is a genetic disorder characterized by the loss of lower motor neurons (LMNs) residing along the length of the entire spinal cord. SMA is caused by a reduction in the expression of the survival motor neuron (SMN) protein that results in denervation of skeletal muscle and significant muscle atrophy. SMN is a ubiquitously expressed protein that functions in U snRNP biogenesis.

In humans there are two very similar copies of the SMN gene termed SMN1 and SMN2. The amino acid sequence encoded by the two genes is identical. However, there is a single, silent nucleotide change in SMN2 in exon 7 that results in the skipping of exon 7 in the majority of the transcripts from this gene. The transcript lacking exon 7 produces a SMN protein that does not effectively self-associate and is rapidly degraded, leading to low SMN levels. There are however numerous elements within both the SMN1 and SMN2 genes that regulate the incorporation of SMN exon 7. The resulting truncated protein, called SMN7, is less stable and rapidly degraded. The remaining 10-20% of transcript from SMN2 encodes the full length SMN protein. Disease results when all copies of SMN1 are lost, leaving only SMN2 to generate full length SMN protein. Accordingly, SMN2 acts as a phenotypic modifier in SMA in that patients with a higher SMN2 copy number generally exhibit later onset and less severe disease.

Therapeutic approaches for SMA have mainly focused on developing drugs for increasing SMN levels or enhancing residual SMN function. Despite years of screening, prior to the invention disclosed herein, no drugs have been fully effective for increasing SMN levels as a restorative therapy. Of particular interest are negative regulatory sequences which, as a general rule bind hnRNPA1—a negative regulator of splicing. Herein it is demonstrated that when morpholino antisense oligonucleotides complexed with Iohexyl are delivered into the CSF to neurons at a single dose, they can markedly increase survival of SMA mice. Indeed, when delivered in the CSF the disclosed composition shows clearly superior performance and less toxicity compared to other oligonucleotide chemistries. Thus the disclosed compositions are the optimal antisense oligonucleotide chemistry for treatment of SMA is morpholino.

The copy number of SMN2 inversely correlates with patient severity and increased full-length SMN from an SMN2 gene also correlates with a milder phenotype. Thus restoring SMN levels at the correct time should have a major impact on the SMA phenotype in humans. The human SMN2/SMN1 gene contains numerous sequences which regulate the incorporation of SMN exon 7. In particular, intron 6 and 7 contain negative regulatory sequences that in general bind hnRNP1 and encourage skipping of exon 7. These regulatory sequences can be blocked by an antisense oligonucleotide (ASO) thus encouraging the incorporation of SMN exon 7 in SMN2.

ALS is another disease that results in loss of muscle and/or muscle function. First characterized by Charcot in 1869, it is a prevalent, adult-onset neurodegenerative disease affecting nearly 5 out of 100,000 individuals. ALS occurs when specific nerve cells in the brain and spinal cord that control voluntary movement gradually degenerate. Within two to five years after clinical onset, the loss of these motor neurons leads to progressive atrophy of skeletal muscles, which results in loss of muscular function resulting in paralysis, speech deficits, and death due to respiratory failure.

The genetic defects that cause or predispose ALS onset are unknown, although missense mutations in the SOD-1 gene occurs in approximately 10% of familial ALS cases, of which up to 20% have mutations in the gene encoding Cu/Zn superoxide dismutase (SOD1), located on chromosome 21. SOD-1 normally functions in the regulation of oxidative stress by conversion of free radical superoxide anions to hydrogen peroxide and molecular oxygen. To date, over 90 mutations have been identified spanning all exons of the SOD-1 gene. Some of these mutations have been used to generate lines of transgenic mice expressing mutant human SOD-1 to model the progressive motor neuron disease and pathogenesis of ALS. In one aspect, disclosed herein are method of treating ALS comprising administering to a patient in need of said treatment a composition comprising an antisense oligonucleotide and a non-ionic, low-osmolar contrast agent, wherein the antisense oligonucleotide binds to a mutated SOD1 gene.

SMA and ALS are two of the most common motor neuron diseases. Recent work in rodent models of SMA and ALS has examined treatment by gene delivery using viruses that are retrogradedly transported following intramuscular injection. Clinical use of such treatments may be difficult given the numerous injections required to target neurodegeneration throughout the spinal cord, brainstem and motor cortex.

The antisense oligonucleotide containing compositions disclosed herein avoid problems of prior therapeutic efforts by correcting masking or correcting the genetic aberrations that result in many of these disease. For example, a number of other disorder have inefficient production of full length transcript such as, for example, Friedreich's ataxia and Familial dysautonomia (FD). In this case blocking of a negative regulator or antisense transcript can enhance the production of full length transcript and thus ameliorate the disorder. In the case of repeat expansion disorders such as myotonic dystrophy or Amytrophic lateral sclerosis (ALS)/ Front temporal deminanta (FTD) either expansion of a CTG repeat (myotonic) or in ALS/FTD a GGGGCC repeat can form aggregates and bind RNA binding proteins an antisense oligonucleotide (morpholino) to the repeat can displace these proteins from the RNA aggregate and restore function by realizing these proteins from the aggregate repeat RNA.

Lastly there are dominant genes causing neurological disorder sometimes by gain of function. Huntington's disease, spinobubular muscular atrophy (SBMA) and many of the spinocerebellar ataxias are caused by expansion of a CAG repeat which encodes glutamine which gives toxic properties to this allele. Knockdown of expression for instance by inducing exon skipping such that the translation reading frame is disrupted stops the production of protein and can stimulate nonsense mediated decay of the mRNA thus reducing the toxic protein load. In addition there are disorders such as Parkinson's due to overexpression of alpha-synuclein or the expression of mutant SOD1, TDP43 that gives rise to ALS in this case antisense oligonucleotides of the morpholino chemistry can be delivered complexed to iohexyl in order to skip and exon so the resulting reading frame of the RNA is disrupted or by blocking translational initiation this results in reduction of the toxic protein.

Accordingly, in one aspect, disclosed herein are methods of treating a neurodegenerative disease in a patient in need thereof comprising administering to the patient a composition comprising an antisense oligonucleotide and a non-ionic, low-osmolar contrast agent to the patient. As it disclosed throughout the specification, the ASO can be an siRNA, shRNA, or morpholino. It is understood and herein contemplated that the ASO can rescue a healthy phenotype by disrupting translation, binding to a target nucleotide, inducing exon skipping, blocking an intron splice silencer, blocking an exon splice enhancer, binding to a repeat nucleotide sequence, or blocking binding to a sequence in toxic RNA. In one aspect, the ASO of the disclosed methods comprises a morpholino that binds to a SMN, a mutated SOD1 gene, C9orf72 repeats, alpha-synuclein, DMPK repeats, ZNF9 repeats, CAG repeats, CTG repeats, CCTG repeats, GGGGCC repeats, or a negative regulatory element in intro 6 or intron 7 of SMN2. In one aspect, disclosed herein are methods of treating SMA, wherein the morpholino can bind SMN2 between nucleotides 67 and 112, upstream of exon 7 (E1) or SMN2 10 nucleotides downstream of exon 7 (intronic splicing silencer N1 (ISS-N1)). For example, the morpholino can bind to a nucleic acid comprising SEQ ID NO: 1 or a fragment thereof at least 15 nucleotides long. In one aspect, disclosed herein are methods of treating SMA comprising administering to a patient in need thereof a composition comprising a morpholino and a non-ionic, low-osmolar contrast agent, wherein the morpholino comprises the sequence set forth in SEQ ID NO: 4, SEQ ID NO: 5, SEQ ID NO: 6, or SEQ ID NO: 7. It is understood and herein contemplated that any non-ionic, low-osmolar contrast agent described herein can be used in the disclosed methods including, but not limited to iobitridol, iohexyl, iomeprol, iopamidol, iopentol, iopromide, ioversol or ioxilan. Thus, for example disclosed herein are methods of treating SMA comprising administering to a subject a morpholino comprising the sequence as set forth in SEQ ID NO: 5 an iohexyl.

It is further contemplated herein that the disclosed treatment methods and compositions can be used in conjunction with other known agents. Thus, combination therapies are also contemplated by the invention. Combination as used herein includes both simultaneous treatment or sequential treatments. Combinations of methods of the invention with standard medical treatments (e.g., riluzole in ALS) are specifically contemplated, as are combinations with novel therapies.

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Figure 2A:
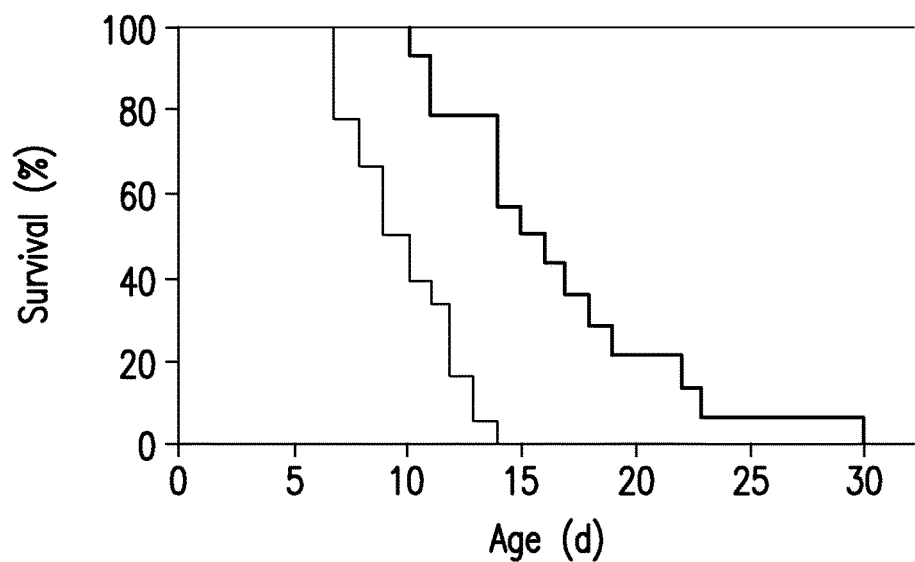
FIG. 2A shows ICV injection of scrambled control MOE (red) or 20 μg/g of splicing correcting MOE into SMA mice. (Green). Average survival is 23 days.

Morpholino Antisense Oligonucleotide for the Treatment of Spinal Muscular Atrophy Two antisense morpholinos against the ISS-N1 sequence have been developed. The first is a 20mer of the following sequence: ATTCACTTTCATAATGCTG (SEQ ID NO: 5). The results from studies in SMA delta7 mice using this ASO have been published in Porensky, et al, 2012, Human Molecular Genetics, which in herein incorporated by reference. The ASO composition increases incorporation of SMN exon 7 resulting in increased full-length SMN transcript levels and increased SMN protein. The ASO composition was tested at various dosages in the SMA delta7 mice for ability to rescue the SMA phenotype. The survival of SMA animals treated with MOE ASO (developed by ISIS Pharmaceuticals, Inc.), when delivered via ICY, is compared to the disclosed 20mer morpholino composition in FIG. 2. FIG.

Figure 2B:
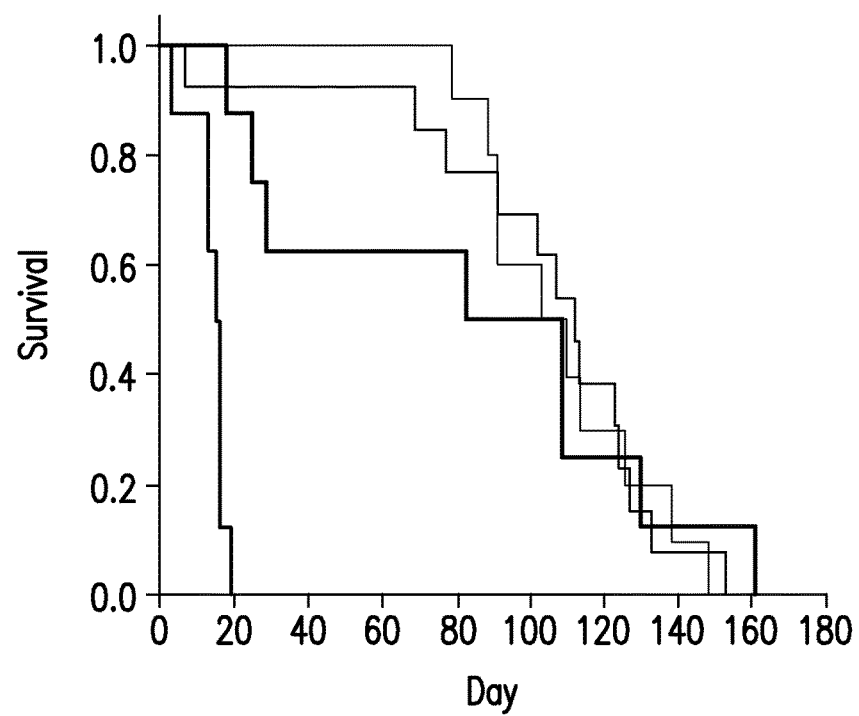
FIG. 2B shows ICV injection of scrambled control MO (yellow) or MO ASO at 27 μg (black), 54 μg (red) 83 μg (blue).
Figure 2C:
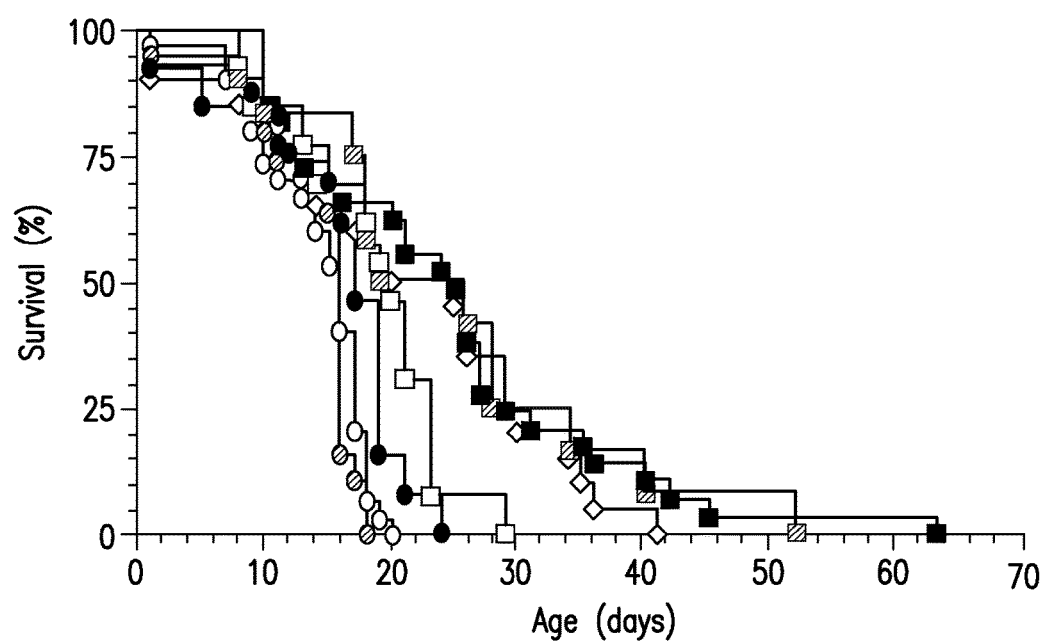
FIG. 2C shows 4 μg/g MOE (blue square) and 8 μg/g MOE (pink diamond) delivered by ICV. Circles are untreated or scrambled ASO controls.
Figure 3A:
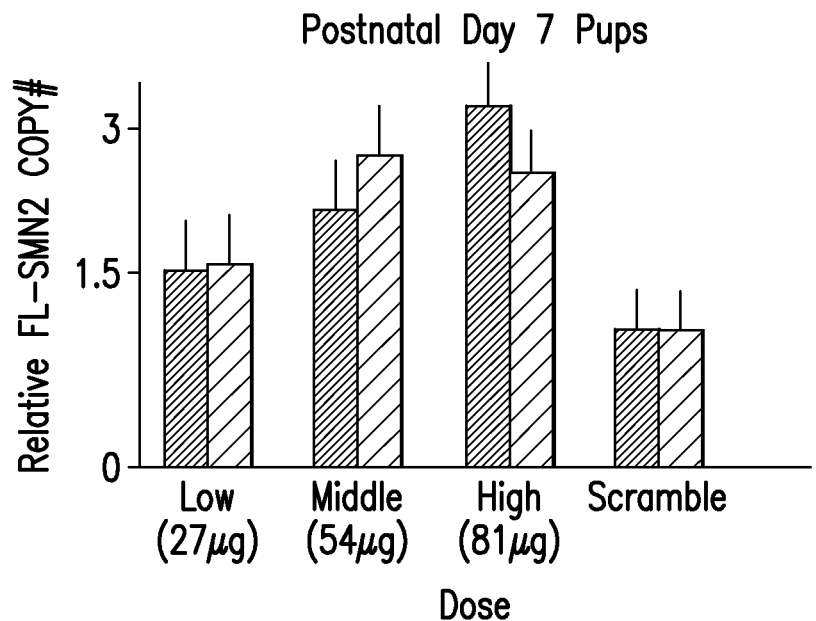
FIG. 3A shows ddPCR for relative amount of full-length SMN at varying dose of morpholino ASO. The primers are SMN2 specific.
Figure 3B:
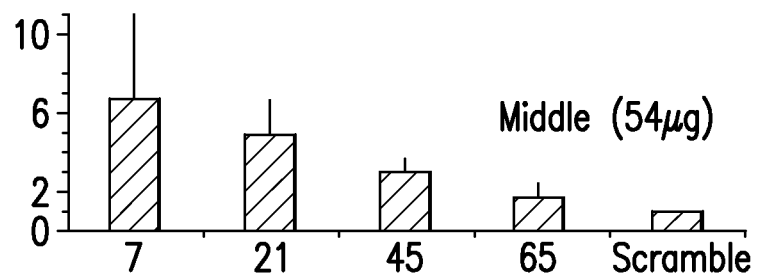
FIG. 3B shows Quantitative RT-PCR for full-length SMN in spinal cord P7-65 of Middle (54 ug) dose morpholino ASO injected at PND1
Figure 3C:
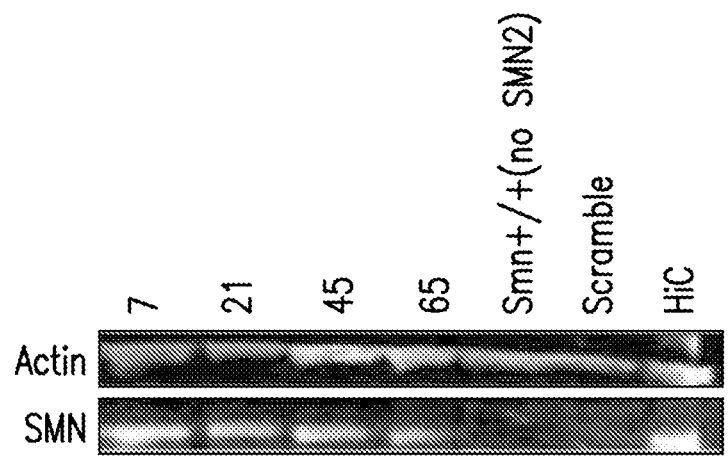
FIG. 3C shows the SMN protein level in SMA mice brain after 27 ug ASO injection.
Figure 3D:
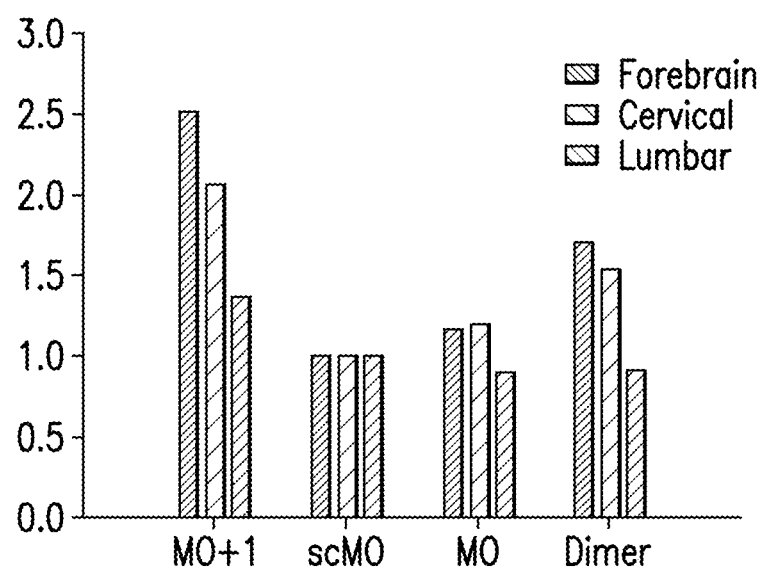
FIG. 3D shows ddPCR of SMN2 full-length transcript after ICV delivery in adult animals. scMO: scrambled control, MO: naked morpholino, Dimer: morpholino annealed to a complementary DNA oligonucleotide to give a negative charge (mimicking an MOE which has a negative charge), MO+1: morpholino complexed with Iohexyl note the increased delivery to all areas of the spinal cord including the lumbar region.

2A shows the data reported by Hua et al using the ASO MOE. The dose of the 18mer MOE used was 20 µg/g and the mice were injected at PND1. The mice at PND1 are approximately 1.5 g, thus this is a dose of 30 µg. The mice that were injected have two copies of SMN2 and a deletion allele that can produce mouse Smn lacking exon 7. They live an average of 10 days. The mean survival on treatment with the 18mer MOE is a relatively small increase to 17 days. This contrasts with the data obtained with the disclosed ASO morpholino composition in the delta7 SMA mice (FIG. 2B). With the low dose of morpholino composition (27 µg) the mean and median survival is increased from 14 to 83 days. Furthermore the increased doses of 53 µg and 81 µg have survival rates of over 100 days with a single ICV dosing and no noted toxicity. Indeed, even at 135 µg no toxicity was noted with the disclosed morpholino composition. This directly contrasts with the results reported in Passini et al using the MOE ASO, also delivered by ICV to the same delta7 mouse model, where 8 µg/g produced toxicity. In this report the optimal concentration of MOE ASO was 4 µg/g which resulted in mean survival of 23 days. The survival curves for these experiments are shown in FIG. 2C. The disclosed morpholino composition has also been dosed at comparable low doses of 5 µg and obtained a higher relative mean survival of 42 days. Thus in the current efficacy model, when delivered by ICV, the disclosed morpholino ASO composition is clearly superior to the MOE ASO both in efficacy (survival) and safety (toxicity).

It can be important to administer the ASO in neonatal humans in an early therapeutic window, for example in Type 1 SMA cases. However, no evidence in the delta7 mice indicates a peripheral requirement for high SMN levels (greater than the levels produced by two copies of SMN2) when using morpholinos. Furthermore, SMA can be completely rescued with an allele that restores SMN expression on expression of Cre that is essentially restricted to the nervous system (McGovern et al., FSMA meeting 2012). Delta7 SMA animals can also be rescued upon morpholino injections into the periphery but this result was clearly due to the morpholino ASO crossing the BBB at these early postnatal time points. The result was no different than that obtained by ICV administration of morpholino. Thus, there is no requirement for increased SMN in the peripheral compartment. Moreover, the recent paper from the Krainer group describing knockdown of SMN, does not indicate a critical peripheral role of SMN outside the central nervous system. This is also the case in a large animal model of SMA. In pigs, an scAAV9-SMN shRNA knockdown approach was used via intrathecal delivery to produce an SMA like phenotype with clearly identified proximal weakness, EMG abnormalities and loss of ventral, but not dorsal, root axons. Finally, it is quite clear that SMA in humans is predominantly a motor neuron disorder thus the CNS must be targeted for an effective therapy.

Data concerning the 20mer ISS-N1 ASO morpholino composition is shown in FIG. 3. First, using digital droplet PCR (ddPCR) it was demonstrated that a dose response curve for the morpholino composition correlates directly to survival of the SMA animals (27 µg=median survival 83 days, 54 µg=median survival 104 days, and 83 µg=median survival 112 days). ddPCR is a relatively new technique which is more reliable than real-time PCR. The PCR reaction is partitioned into droplets and then each droplet is amplified individually and counted as positive or negative for probe fluorescence. The number of positive droplets conforms to a Poisson distribution and is proportional to the initial template DNA concentration. (DNA concentration is titrated such that each droplet contains one or less templates). In FIG. 3A, the ASO composition doses (administered at PND1) are assayed for full-length SMN at PND7 relative to cyclophilin mRNA. There is a clear increase in the amount of full-length SMN with each dose of morpholino. There is also an increase in full-length SMN at lower doses of morpholino (5 µg and 10 µg). In FIG. 3B the amount of SMN full-length mRNA is determined by quantitative RT-PCR after injection of 54 µg of morpholino at PND1. Tissue samples were taken at PND7, 21, 45 and 65. A steady decay of full-length SMN message is observed and this occurs for all doses of the ASO composition used. The SMN protein levels are shown in FIG. 3C and again show a similar decline in levels over time. The level is still increased over baseline at 65 days yet a boost of ASO at PND30 can further increase survival. This also gives an indication of the importance of frequency of intrathecal injection. Previously, single bolus injections of morpholino were performed at PND30 via stereotactic injection into the ventricle without any marked improvement in survival. However, this initial experiment was done with naked morpholino and in adult animals there is minimal spread of the naked morpholino from the injection site (FIG. 3D). This problem is solved (FIG. 3D) by complexing the morpholino with Iohexyl. This Reagent is compatible with clinical practice and has a known toxicity profile. It can also be noted in FIG. 3D that annealing the morpholino with a complementary DNA molecule resulted in increased delivery, but was not as effective as Iohexyl. The negatively charged clamped morpholino (Dimer) can distribute in a similar manner to MOEs. Thus naked morpholinos do not distribute as widely as MOEs. However, this is easily overcome by the novel addition of Iohexyl. Furthermore, due to their low toxicity, morpholinos can be used at much higher concentrations than MOEs, even when complexed with Iohexyl.

In addition to the ISS-N1 20mer morpholino composition described herein, another ISS-N1 morpholino composition is disclosed. In vitro studies using SMA patient derived fibroblasts determined that a 25mer (−10-34) MO composition (as opposed to the 20mer (−10-29) MO), also optionally complexed with Iohexyl, gave the highest increase in SMN. However the difference in SMN induction, when used at 600 nm, was minimal, (1.86 vs. 2.49 fold increase of SMN). These morpholino compositions have been compared for the ability to rescue survival in the SMA delta7 mouse. In Table 1 the optimized 25mer (−10-34) MO composition is compared to the 20mer (−10-29) MO composition for survival of the delta7 SMA mice. The 2 mM concentration is equivalent to 27 µg of morpholino, 4 mM≈54 µg and 6 mM≈81 ug. After a single ICV injection the time of survival is only slightly extended and not significantly different from the 20mer (−10-29) MO. The dosage profile for survival using the 25mer (−10-34) MO composition is shown in Table 2. The survival of scrambled or untreated delta7 mice was similar to previously reported (mean survival of 13 days).

TABLE 1

Comparison of survival times of mice injected with 25mer (−10-34) MO or 20mer (−10-29) MO

| Comparison of | mean survival time (days) | median survival time (days) | Log Rank test P-value |
|---|---|---|---|
| 2 mM 25mer (−10-34) VS 2 mM 20mer (−10-29) | 99.5 VS 83.0 | 110 VS 83 | 0.543 |

TABLE 1-continued

Comparison of survival times of mice injected with 25mer (−10-34) MO or 20mer (−10-29) MO

| Comparison of | mean survival time (days) | median survival time (days) | Log Rank test P-value |
|---|---|---|---|
| 4 mM 25mer (−10-34) VS 4 mM 20mer (−10-29) | 117.2 VS 111.0 | 110 VS 106 | 0.700 |
| 6 mM 25mer (−10-34) VS 6 mM 20mer (−10-29) | 135.3 VS 102.9 | 126 VS 112 | 0.097 |

TABLE 2

Comparison of mean and median survival time of SMA mice injected with 25mer (−10-34) MO

| Dosage | Mean survival time (days) | 95% CI | Median survival time (days) | 95% CI | Log-Rank test P-Value |
|---|---|---|---|---|---|
| 0.5 mM 25mer (−10-34) | 49.0 | (30.9, 67.01) | 37 | (28.2, 45.8) | <0.001* |
| 1.0 mM 25mer (−10-34) | 72.7 | (39.3, 106.0) | 65 | (11.2, 118.8) | 0.005* |
| 2 mM 25mer (−10-34) | 99.5 | (29.2, 42.3) | 110 | (29.6, 190.4) | 0.03* |
| 4 mM 25mer (−10-34) | 117.2 | (98.7, 135.7) | 106 | (101.7, 110.3) | 0.001* |
| 6 mM 25mer (−10-34) | 135.3 | (108.7, 162.0) | 126 | (97.2, 154.8) | <0.001* |

Thus both the 20mer (−10-29) MO and the 25mer (−10-34) MO compositions produce a strong impact on SMA mice.

Figure 4A:
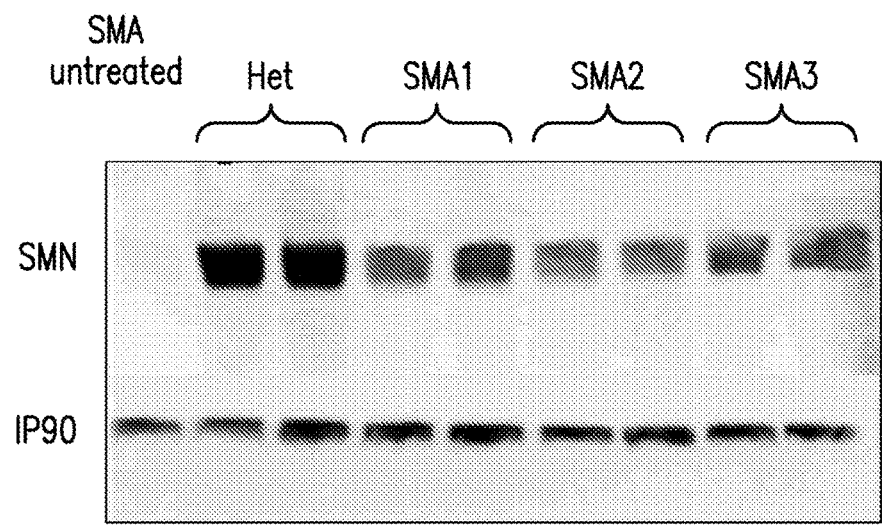
FIG. 4A shows Western blot of spinal cord tissue at PND12 following injection of ASO E1 at PND1 (35 ug).
Figure 4B:
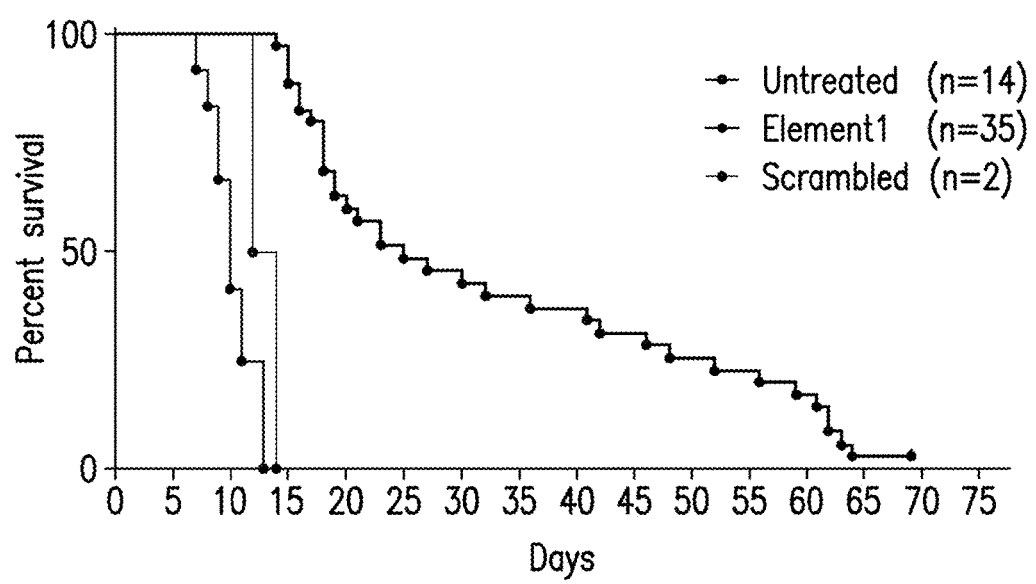
FIG. 4B shows the survival curve of SMA animals following injection of ASO E1 at PND1 (35 ug).

Another MO target lies in intron 6, and is referred to herein as E1. This sequence is not related to ISS-N1. The results of using a 26mer E1 MO ASO composition at 35 µg directed to this intron are shown in FIG. 4. Western blot analysis in FIG. 4A clearly reveals an increase of SMN in spinal cord upon treatment of SMA mice with the 26mer MO. The survival curve for mice treated with 35 µg by ICV at PND1 is shown in FIG. 4B. The mean survival in the delta7 SMA mice is 35 days. This survival rate is less than the 20mer or the 25mer morpholino. However the 26mer E1 morpholino composition still shows improved efficacy when compared to the ICV administration of MOE. Furthermore, the dose of the 26mer can be increased, which is likely to result in increased survival. It is also important that re-dosing at PND30 days with the addition of Iohexyl and morpholino can result in a further improvement in survival.

2. Example 2

Generation of SMA Mice

SMNΔ7 carrier breeding mice (SMN2+/+; Smn+/−; SMNΔ7+/+) were crossed to generate three types of offspring varying in mouse Smn genotype: Smn +/+, Smn +/− and Smn −/− as previously described. All breeding and subsequent use of animals in this study where approved by the IACUC of The Ohio State University, Columbus, Ohio.

3. Example 3

ICV Injections

The P0 or P4 pup was cryo-anesthetized and hand-mounted over a back-light to visualize the intersection of the coronal and sagittal cranial sutures (bregma). A fine-drawn capillary needle with injection assembly was inserted 1 mm lateral and 1 mm posterior to bregma, and then tunneled 1 mm deep to the skin edge (approximating) ipsilateral lateral ventricle. An opaque tracer (Evans blue, 0.04%) was added to the reagent to visualize the borders of the lateral ventricle after injection of 2 µl of morpholino.

4. Example 4

Stereotactic Injections

P30 mice were anesthetized with inhalational isoflurane (3% induction, maintenance 1% mixed with high-flow 100% O2). The animal was placed into the cranial stereotactic frame (Kopf Instruments) with digital coordinate guidance (myNeuroLab), and the anesthesia nose cone was secured. The cranial apex was sterilized and a short midline incision was performed with visualization of bregma and lambda. A small burr hole was drilled and cranial needle with attached Hamilton syringe was guided to preselected coordinates (A/P 0.58 mm, D/L 2.15 mm, M/L 1.10 mm) for right lateral ventricle cannulation, the coordinates were validated by injection of scAAV4-GFP (ependymal localization) in a trial P30 mouse. 18 µg/g of MO or scMO (equivalent to low dose (2 mM) injection in the P0 pups) was injected at a rate of 0.75 µL/min with digital microinjector (KD Scientific). After injection, the needle was withdrawn and skin closed with running suture. Post-surgical care was approved by the IACUC of The Ohio State University, Columbus, Ohio.

5. Example 5

Facial Vein Injection

Facial vein injection on P0 pups was performed as previously described. MO or scMO was dosed at 50 µg/g 6. Example 6

Mouse Genotyping

The SMN2, Smn knockout allele and SMNΔ7 alleles were genotyped as previously described. Tail snips were gathered at P0, each pup was identified by paw tattooing. All genotyping was performed on P0 as described previously.

7. Example 7

RT-PCR and Real-Time RT-PCR Analysis

RNA was isolated from Trizol (Invitrogen) homogenized tissue and purified with the RNeasy kit (Qiagen). RT-PCR was performed as previously described. The SMNΔ7 transgene lacks the terminal portion of exon 8. Primers were designed to amplify only the SMN2 transcripts that contain this region, thus distinguishing SMNΔ7 from SMN2: (hSMN2E8rev) TTATATACTTTTAAACATATAGAAGA-TAG (SEQ ID NO: 8), (hSMNE6fwd) AGATTCTCTTGAT-GATGCTGAATG (SEQ ID NO: 9).

Real-time RT-PCR assayed for full-length SMN2 transcripts relative to cyclophilin. SMN2 amplification: (hSM-NFull Fb) GTTTCAGACAAAATCAAAAAGAAGGA (SEQ ID NO: 10), (hSMNFull Rc) TCTATAACGCTTCA-CATTCCAGATCT (SEQ ID NO: 11), probe: (hSMNFull FAM) ATGCCAGCATTTCTCCTTAATTTAAGG (SEQ ID NO: 12). Cyclophilin: (QcycloF) GTCAACCCCACCGT-GTTCTT (SEQ ID NO: 13), (QcycloR) TTGGAACTTT-GTCTGCAAACA (SEQ ID NO: 14), probe: (Probecyclo NED) CTTGGGCCGCGTCT (SEQ ID NO: 15). PCR reaction for SMN2 used 2 µl cDNA, 0.6 µl (300 nm) forward and reverse primer; cyclophilin, 1.8 µl (900 nM) forward and reverse primer. Transcript level was determined as previously described.

8. Example 8

Digital Droplet PCR cDNA was collected as detailed above. Identical primers and probe were used for ddPCR as was used for real time RT-PCR. The PCR reaction for SMN2 used 1.0 µl cDNA and cyclophilin used 0.1 µl. 1.8 µl (900 nm) forward and reverse primer was used for both SMN2 and cyclophilin. Trancript level was determined by calculating the ratio of SMN2 versus cyclophilin concentration.

9. Example 9

Western

Western blot analysis was performed as previously described. Detection was performed using the LI-COR Odyssey Imaging System (Biosciences) and quantification was determined using Odyssey Infrared Imaging System Application Software (Biosciences).

10. Example 10

Morpholino ASO Preparation

The MO sequence, numbered from the SMN2 exon 7 donor site (FIG. 1), was ATTCACTTTCATAATGCTGG (SEQ ID NO: 6) (MWT=6754, Gene Tools). scMO sequence was TCCTTTAAAGTATTGTGACC (SEQ ID NO: 7) (MWT=6754, Gene Tools). Morpholinos were resuspended in sterile 0.9% sodium chloride, aliquoted, and mixed with Evans Blue (final concentration 0.04%). Three different molar concentrations were prepared (High: 6 mM=40.5 µg/µL; Middle: 4 mM=27 µg/µL; Low: 2 mM=13.5 µg/µL). Stock solutions were stored at −20° C., working solutions at 4° C. Lissamine tagged morpholino (sequence CCTCTTACCTCAGTTACAATTTATA) (SEQ ID NO: 16) was resuspended to 2 mM in 0.9% NaCl. 2 µl of morpholino oligomer was injected, yielding total doses per animal of 81 µg (High), 54 µg (Middle) and 27 µg (Low).

11. Example 11

SMN Immunofluorescence

SMNΔ7 SMA mice (SMN2+/+; HB9:GFP; Smn−/−; SMNΔ7+/+) were injected by P0 ICV with 4 mM MO. Carrier control was not injected. Spinal cords were harvested, frozen, fixed and sectioned at P7 as previously described. Tissue sections were stained with anti-human SMN KH antibody 1:10 overnight and Alexa Fluor® 594 goat anti-rabbit IgG (Molecular probes) (1:1000). Endogenous lissamine (RFP) and GFP fluorescence were imaged with a Nikon E800 Eclipse fluorescent microscope, Ultrapix Digital Camera (Olympus) with MagnaFIRE v2.1C software (Optronics), and further processed with Adobe Photoshop CS2.

12. Example 12

Both disclosed ISS-N1 directed ASO compositions have demonstrated that there is a dose response curve in survival of the SMA delta7 animals. However, there are at least two potentially positive effects of higher dosing: one, increased alteration of SMN2 and thus higher SMN levels and/or; two, increased levels of MO that is sufficient for rescue for a longer duration. A repeat dosing paradigm with a new ASO administration formulation comprising Iohexyl has been optimized to obtain delivery of the MO throughout the spinal cord in the adult animal. Thus, mice receive an initial dose of MO ASO at PND1 (date of birth) followed by a continual 4 week dose of MO ASO via an osmotic pump cannulated into the ventricle. The level of MO in tissue is measured under each condition. This allows for the determination of MO ASO dose that gives the greatest effect on survival of delta7 mouse.

a) Production of Morpholino Oligonucleotide

The ISS-N1 20mer (−10-29) MO and ISS-N1 25mer (−10-30) MO (referred to herein as the two ISS-N1 MOs) as well as the intron 6 targeted 26mer E1 MO can be synthesized as described herein.

b) Dosing Mice

All studies can be carried out using SMA affected mice which are generated by crossing the carrier parents which are heterozygous for the mouse knockout allele and homozygous for all other transgenes (SMN2+/+, SMND7+/+, Smn+/−). At PND1 (here defined as date of birth, equivalent to P0) pups can be tattooed and genotyped with a rapid genotyping protocol. Briefly mothers are temporally moved to separate housing. The appropriate dose of morpholino (54 µg/g, 36 µg/g, 18 µg/g, 3.3 µg/g) can be mixed with isotonic saline and Iohexyl in a siliconized microfuge tube. The cryo-athesthetized pup can be hand-mounted over a backlight. A fine-drawn capillary needle with an injection assembly can be inserted 1 mm lateral and 1 mm posterior to bregma and then tunneled 1 mm deep to the skin edge (approximately) into the ipsilateral lateral ventricle. An opaque tracer (Evans blue 0.04%) can be added to the reagent to visualize the borders of the lateral ventricle after injection. The volume of injection may not exceed 2 µl and animals that do not receive proper injections can be excluded from analysis. A scrambled oligonucleotide and equivalent concentration can be used as control.

All litters are culled to at most 5 animals to keep a consistent size of litter for feeding. The injector and evaluator are blinded to genotype of the animals and the randomization of litters is performed independently. In the case of the E1 MO, a group of 10-15 SMA animals can first have survival assessed after a single ICV injection for survival. This survival curve has already been established for the two ISS-N1 MOs. A second group of E1 MO injected SMA mice can be used for re-administration of the MO at PND30 (re-administration procedure described below).

PND30 mice can be anesthetized with inhalational isoflurane (mixed with high flow 100% $O_2$) at 3-5% for induction and 2-5% for maintenance. The animal can be placed in a cranial stereotactic frame with digital coordinate guidance and the anesthesia nose cone secured. The mouse can be secured to the stereotactic system with bilateral pins entering the external auricular canal, as well as with a rostral nose cone. The cranial midline can be shaved from bregma to lambda, and the skin can be prepared with betadine. The skin can be incised and periosteum elevated to reveal suture lines. The cranium can be leveled to ensure that bregma and lambda lay within the same axial plane. The stereotactic system, with attached nanoinjector and cranial probe, can be zeroed over bregma. Intraventricular delivery can be achieved by delivery to a set of predetermined coordinates in the x/y/z axes with respect to bregma [Paxinos et al. The Mouse Brain in Stereotaxic Coordinates: Compact Second Edition, Second Edition. 2004 Elsevier Science]. A craniotomy can be created with a high-speed burr over the aforementioned entry point, and the stereotactic probe can then be inserted into the ipsilateral lateral ventricle. After cannulation of the cerebral ventricle, the implanted cannula can be connected to a tunneled catheter leading to the subcutaneous osmotic pump implanted in the dorsal intrascapular area of the mouse. A subcutaneous pocket can be created adjacent to but not underneath the skin incision to ensure proper wound healing and avoidance of wound breakdown. Surgical preparation of the intrascapular site can be identical to the cranial prep. The incision can be closed with interrupted full thickness absorbable suture. The flow rate can be variable depending on predetermined settings, for example, 0.11 µl/hr (4 week maximum) and the total dose for a starting dose of 18 ug/g can be (18 ug/g+44.8 ug/g). For each of the starting doses the concentration of the MO in the osmotic pump can be adjusted. Thus a lower concentration is used for the lower initial dose. The complete amount of MO delivered over time can be recorded. The survival of the animals per complete dose of MO can be determined. The MO can be mixed with Iohexyl which increases distribution of the MO throughout the CNS and results in alteration of SMN2 at all levels of the spinal cord.

c) Re-administration of the Morpholino

The level of MO in tissue samples at specific time points can be determined. Five mice at each dose can be analyzed at PND7, an additional 5 animals per dose can analyzed 7 days after the complete dose has been dispersed by the osmotic pump (at approximately 9 weeks). The spinal cord and brain can be harvested from the mice. One section of spinal cord (lumbar) and brain can be used for determination of the amount of full-length SMN produced from SMN2 by digital droplet PCR (ddPCR). The thoracic section of the spinal cord and the other half of the brain can be used to determine the amount of MO in tissue by the method previously described by Devi et al. Briefly, a tissue extract is made and the sample complexed with a short complementary sense strand probe that is fluorescein labeled at its 5 prime end. A set of standards can be created by spiking a sample that has not received morpholino treatment with 10-1000 ng of MO along with an internal standard. The samples can then be analyzed by HPLC with injection onto a Dionex DNA Pac PA-100 column and HPLC machine equipped with a fluorescent detector. The resulting peak gives the amount of ASO in the sample. The system can be altered to use mass spectrometry, for instance using MALDI-TOF with a sinapinic acid matrix, however this has not to date been reported in the literature for measurement of morpholino levels in tissues.

d) Measurement of MO Level and SMN2 Splicing

The ddPCR can be performed and used to quantify the amount of full-length SMN produced at the time points indicated above (PND7 and 9 weeks). Thus the dose of MO can maintain SMN levels above that produced by two copies of SMN2. The aim can be to keep SMN levels above that which was observed at PND45 following a single PND1 injection of the middle dose of MO (FIG. 3). Between PND21 and PND45 the SMN level can be approximately 3 times the level of SMN produced by two copies of SMN2. Previously this level of SMN has been shown to have a major impact on survival of SMA mice.

e) EMG Measurement in Corrected Mice:

Electromyography (EMG) can be performed on rescued SMA mice. Briefly the EMG can be performed as early as PND6 with high reliability. This technique can also be performed in neonatal mice. Small loop electrodes can be used and the fur can be removed to allow good contact with the skin. Stimulation occurs through the sciatic notch and the Incremental stimulation method can be used for motor unit number estimation (MUNE). SMA delta7 mice show relatively normal MUNE at PND6 with a severe drop in MUNE at PND8 followed by a shallow slope out to the animal's death at PND14. The MUNE assay can be advantageous because this technique measures the entire motor circuit, and furthermore, MUNE can be used on patients in clinical trials as an outcome measure. In the MO treated delta7 SMA mice examination of later ages (PND21) can determine if any differences occur between the different dosage groups. Furthermore, the motor neurons that do survive can sprout to compensate, thus they show a large Compound Muscle Action Potential (CMAP) but a small MUNE.

13. Example 13

Dosing of Morpholino ASO Compositions

The ISS-N1 targeted MO composition that demonstrates the greatest efficacy and the E1 MO compositions can be tested in Cynomolgus Macaques for level of MO obtained in tissue after 3 intrathecal injections at PND1, PND30 and PND60. The aim is to determine if a sufficient level of MO can be achieved after repeated dosing at 4 week intervals. The volume of cerebrospinal fluid (CSF) in a mouse is considerably less than the volume of CSF in a human. Human neonates have approximately 50 ml of CSF (15 mls/kg) and adult humans have 150 ml (2 ml/kg). In mice the volume of CSF in an adult is 40 µl (2 µl/g), the same ratio as an adult human. If one assumes a similar scaling in mice, then a PND1 mouse that weighs 1.5 g has approximately 22 µl of CSF. Therefore, if the middle dose of MO (54 µg) is used divided by 22 µl of CSF is 2.45 µg/µl or 300 mg for a neonatal human. No reliable data on the CSF volume for the Cynomolgus Macaque has been found and an adult is said to have 1/10 volume of a human i.e. 15 mls.

a) Morpholino Synthesis:

The two MOs can be synthesized by Sarepta Therapeutics. To date the ISS-N1 25mer (−10-30) MO shows a slight increase in survival of delta7 SMA mice when compared to the ISS-N1 20mer (−10-29) MO, but the difference is not statistically significant. The critical parameter in the efficacy of the MO is the length of time SMN levels remains above the critical threshold, thus re-dosing of the MO can overcome any minor difference between the 25mer MO and the 20mer MO. Morpholino ASOs can be synthesized by methods known in the art.

b) Procedure for Dosing Cynomolgus Macaques:

As discussed in background, there is evidence that early induction of SMN is beneficial for treatment of SMA. Thus, intrathecal injection of the MO compositions can be performed in neonatal Cynomolgus Macaques. The injection procedure is briefly described as follows: The subject can be lightly sedated with ketamine or telzaol and the lumbar spine region can be shaved. The immobilized animal can have the spine flexed and the catheter introduced between L3 and L4. The morpholino can be intrathecally injected at three time periods 4 weeks apart (PND1, PND30 and PND60). CSF can be drawn at each time point at an equivalent volume to the injected MO. Specifically, CSF can be drawn both prior to and 15 minutes after injection of the ASO at each injection. Thus, the first sample of CSF has no MO and in the second draw, 15 minutes after injection, the sample has MO mixed with CSF. The distribution of MO throughout the CSF can be relatively fast based on observation of radiopaque die mixing. This sample can be used to determine the initial dose of MO per ml of CSF. The initial total CSF volume can be determined by MRI. The subsequent intrathecal injections follow the same paradigm to determine how much morpholino is left in the CSF from the previous injection, as well as determining the amount of the additional MO dose.

c) Measurement of Morpholino Level:

The measurement of the MO in Macaques with HPLC and fluorescent detection can be the same as described in Example 1. The level of morpholino in tissue can be correlated with the levels found in mouse spinal cord to determine suitable MO dose. The decay and accumulation of MO can also be measured to determine $C_{max}$. The distribution of MO can be determined by insitu hybridization G. References 1. Lefebvre, S. et al. Identification and characterization of a spinal muscular atrophy-determining gene. *Cell* 80, 155-165 (1995).
2. Burghes, A. H. & Beattie, C. E. Spinal muscular atrophy: why do low levels of survival motor neuron protein make motor neurons sick? *Nat Rev Neurosci* 10, 597-609 (2009).
3. Lorson, C. L., Hahnen, E., Androphy, E. J. & Wirth, B. A single nucleotide in the SMN gene regulates splicing and is responsible for spinal muscular atrophy. *Proc Natl Acad Sci USA* 96, 6307-6311 (1999).
4. Monani, U. R. et al. A single nucleotide difference that alters splicing patterns distinguishes the SMA gene SMN1 from the copy gene SMN2. *Hum Mol Genet.* 8, 1177-1183 (1999).
5. Cartegni, L. & Krainer, A. R. Disruption of an SF2/ASF-dependent exonic splicing enhancer in SMN2 causes spinal muscular atrophy in the absence of SMN1. *Nat Genet.* 30, 377-384 (2002).
6. Kashima, T. & Manley, J. L. A negative element in SMN2 exon 7 inhibits splicing in spinal muscular atrophy. *Nat Genet.* 34, 460-463 (2003).
7. Gennarelli, M. et al. Survival motor neuron gene transcript analysis in muscles from spinal muscular atrophy patients. *Biochem Biophys Res Commun* 213, 342-348 (1995).
8. Parsons, D. W. et al. An 11 base pair duplication in exon 6 of the SMN gene produces a type I spinal muscular atrophy (SMA) phenotype: further evidence for SMN as the primary SMA determining gene. *Hum Mol Genet.* 5, 1727-1732 (1996).
9. Lefebvre, S. et al. Correlation between severity and SMN protein level in spinal muscular atrophy. *Nat Genet.* 16, 265-269 (1997).
10. Coovert, D. D. et al. The survival motor neuron protein in spinal muscular atrophy. *Hum Mol Genet.* 6, 1205-1214 (1997).
11. Lorson, C. L. & Androphy, E. J. An exonic enhancer is required for inclusion of an essential exon in the SMA-determining gene SMN. *Hum Mol Genet.* 9, 259-265 (2000).
12. Lorson, C. L. et al. SMN oligomerization defect correlates with spinal muscular atrophy severity. *Nat Genet.* 19, 63-66 (1998).
13. Burnett, B. G. et al. Regulation of SMN protein stability. *Mol Cell Biol* 29, 1107-1115 (2009).
14. McAndrew, P. E. et al. Identification of proximal spinal muscular atrophy carriers and patients by analysis of SMNT and SMNC gene copy number. *Am J Hum Genet.* 60, 1411-1422 (1997).
15. Mailman, M. D. et al. Molecular analysis of spinal muscular atrophy and modification of the phenotype by SMN2. *Genet Med* 4, 20-26 (2002).
16. Feldkotter, M., Schwarzer, V., Wirth, R., Wienker, T. F. & Wirth, B. Quantitative analyses of SMN1 and SMN2 based on real-time lightCycler PCR: fast and highly reliable carrier testing and prediction of severity of spinal muscular atrophy. *Am J Hum Genet.* 70, 358-368 (2002).
17. Prior, T. W. et al. A positive modifier of spinal muscular atrophy in the SMN2 gene. *Am J Hum Genet.* 85, 408-413, (2009).
18. Bebee, T. W., Gladman, J. T. & Chandler, D. S. Splicing regulation of the survival motor neuron genes and implications for treatment of spinal muscular atrophy. *Front Biosci* 15, 1191-1204, (2011).
19. Hua, Y. et al. Antisense correction of SMN2 splicing in the CNS rescues necrosis in a type III SMA mouse model. *Genes Dev* 24, 1634-1644, (2010).
20. Burghes, A. H. & McGovern, V. L. Antisense oligonucleotides and spinal muscular atrophy: skipping along. *Genes Dev* 24, 1574-1579, (2010).
21. Passini, M. A. et al. Antisense oligonucleotides delivered to the mouse CNS ameliorate symptoms of severe spinal muscular atrophy. *Sci Transl Med* 3, 72ra18, (2011).
22. Monani, U. R. et al. The human centromeric survival motor neuron gene (SMN2) rescues embryonic lethality in Smn(−/−) mice and results in a mouse with spinal muscular atrophy. *Hum Mol Genet.* 9, 333-339 (2000).
23. Hsieh-Li, H. M. et al. A mouse model for spinal muscular atrophy. *Nat Genet.* 24, 66-70 (2000).
24. Le, T. T. et al. SMNDelta7, the major product of the centromeric survival motor neuron (SMN2) gene, extends survival in mice with spinal muscular atrophy and associates with full-length SMN. *Hum Mol Genet.* 14, 845-857 (2005).
25. Le, T. T. et al. Temporal requirement for high SMN expression in SMA mice. *Hum Mol Genet.* 20, 3578-3591, (2011).
26. Lutz, C. M. et al. Postsymptomatic restoration of SMN rescues the disease phenotype in a mouse model of severe spinal muscular atrophy. *J Clin Invest* 121, 3029-3041, (2011).
27. Gavrilina, T. O. et al. Neuronal SMN expression corrects spinal muscular atrophy in severe SMA mice while muscle-specific SMN expression has no phenotypic effect. *Hum Mol Genet.* 17, 1063-1075 (2008).

28 Hua, Y. et al. Peripheral SMN restoration is essential for long-term rescue of a severe spinal muscular atrophy mouse model. *Nature* 478, 123-126, (2011).
29 Porensky, P. N. et al. A single administration of morpholino antisense oligomer rescues spinal muscular atrophy in mouse. *Hum Mol Genet.* 21, 1625-1638, (2012).
30 Ellett, F. & Lieschke, G. J. Zebrafish as a model for vertebrate hematopoiesis. *Curr Opin Pharmacol* 10, 563-570, (2010).
31 Cirak, S. et al. Exon skipping and dystrophin restoration in patients with Duchenne muscular dystrophy after systemic phosphorodiamidate morpholino oligomer treatment: an open-label, phase 2, dose-escalation study. *Lancet* 378, 595-605, (2011).
32 Kinali, M. et al. Local restoration of dystrophin expression with the morpholino oligomer AVI-4658 in Duchenne muscular dystrophy: a single-blind, placebo-controlled, dose-escalation, proof-of-concept study. *Lancet Neurol* 8, 918-928, (2009).
33 Sazani, P. et al. Repeat-Dose Toxicology Evaluation in Cynomolgus Monkeys of AVI-4658, a Phosphorodiamidate Morpholino Oligomer (PMO) Drug for the Treatment of Duchenne Muscular Dystrophy. *Int J Toxicol* 30, 313-321, (2011).
34 Singh, N. K., Singh, N. N., Androphy, E. J. & Singh, R. N. Splicing of a critical exon of human Survival Motor Neuron is regulated by a unique silencer element located in the last intron. *Mol Cell Biol* 26, 1333-1346, (2006).
35 Sahashi, K. et al. TSUNAMI: an antisense method to phenocopy splicing-associated diseases in animals. *Genes Dev* 26, 1874-1884, (2012).
36 Devi, G. R. et al. In vivo bioavailability and pharmacokinetics of a c-MYC antisense phosphorodiamidate morpholino oligomer, AVI-4126, in solid tumors. *Clinical cancer research: an official journal of the American Association for Cancer Research* 11, 3930-3938, (2005).
37 Arora, V., Knapp, D. C., Reddy, M. T., Weller, D. D. & Iversen, P. L. Bioavailability and efficacy of antisense morpholino oligomers targeted to c-myc and cytochrome P-450 3A2 following oral administration in rats. *Journal of pharmaceutical sciences* 91, 1009-1018 (2002).
38 Amantana, A. & Iversen, P. L. Pharmacokinetics and biodistribution of phosphorodiamidate morpholino antisense oligomers. *Curr Opin Pharmacol* 5, 550-555, (2005).

What is claimed is:

1. A composition comprising an antisense oligonucleotide complexed to a non-ionic, low-osmolar contrast agent.

2. The composition of claim 1, wherein the low-osmolar contrast agent is iobitridol, iohexol, iomeprol, iopamidol, iopentol, iopromide, ioversol or ioxilan.

3. The composition of claim 2, wherein the non-ionic, low-osmolar contrast agent is iohexol.

4. The composition of claim 1, wherein the antisense oligonucleotide is a morpholino, siRNA, or shRNA.

5. The composition of claim 4, wherein the antisense oligonucleotide disrupts translation, binds to a target nucleotide, induces exon skipping, blocks an intron splice silencer, blocks an exon splice enhancer, binds to a repeat nucleotide sequence, or blocks binding to a sequence in toxic RNA.

6. The composition of claim 1, wherein the antisense oligonucleotide is a morpholino that binds to a survival motor neuron (SMN) gene, a mutated SOD1 gene, C9orf72 repeats, alpha-synuclein, dystrophia myotonic protein kinase gene (DMPK) repeats, Zinc Finger Protein 9 (ZNF9) repeats, a negative regulatory element in intro 6 or intron 7 of SMN2.

7. The composition of claim 1, wherein the morpholino comprises the sequence set forth in SEQ ID NO: 5, SEQ ID NO: 6, or SEQ ID NO: 7.

8. A method of delivering an antisense oligonucleotide to a tissue, organ, or system in a subject comprising administering to the subject the composition of claim 1.

9. A method of treating a neurological disease in a patient in need thereof comprising administering to the patient the composition of claim 1.

10. The method of claim 9, wherein the neurological disease is selected from the group consisting of Alzheimer's disease, Spinal muscular atrophy (SMA), Myotonic dystrophy, Huntington's disease, Parkinson's disease, Spinocerebellar degeneration, Spinocerebellar ataxia, Friedreich's ataxia, Ataxia telangiectasia, amyotrophic lateral sclerosis, Charcot-Marie-Tooth disease, Vasomotor ataxia, Vestibulocerebellar, Ataxiadynamia, Ataxiophemia, Amyotrophic lateral sclerosis, and Olivopontocerebellar atrophy.

* * * * *

UNITED STATES PATENT AND TRADEMARK OFFICE
CERTIFICATE OF CORRECTION

PATENT NO. : 9,725,716 B2
APPLICATION NO. : 14/363670
DATED : August 8, 2017
INVENTOR(S) : Arthur Burghes et al.

Page 1 of 1

It is certified that error appears in the above-identified patent and that said Letters Patent is hereby corrected as shown below:

Column 1, Lines 14-16, cancel the text beginning with "This work was supported" to and ending "certain rights in the invention." and insert the following language:

--This invention was made with government support under RC2 NS069476 and R01 HD060586 awarded by the National Institutes of Health. The government has certain rights in the invention.--

Signed and Sealed this
Thirteenth Day of November, 2018

Andrei Iancu
*Director of the United States Patent and Trademark Office*

UNITED STATES PATENT AND TRADEMARK OFFICE
CERTIFICATE OF CORRECTION

PATENT NO. : 9,725,716 B2
APPLICATION NO. : 14/363670
DATED : August 8, 2017
INVENTOR(S) : Arthur Burghes, Paul Porensky and Brian Kaspar Page 1 of 1

It is certified that error appears in the above-identified patent and that said Letters Patent is hereby corrected as shown below:

In the Specification

Column 1, Lines 14-16 replace the Government Support Clause with:
--This invention was made with government support under grant numbers NS069476, and HD060586 awarded by the National Institutes of Health. The government has certain rights in the invention.--

This certificate supersedes the Certificate of Correction issued November 13, 2018.

Signed and Sealed this
Twentieth Day of October, 2020

Andrei Iancu
*Director of the United States Patent and Trademark Office*